(12) United States Patent
Blower et al.

(10) Patent No.: US 11,866,406 B2
(45) Date of Patent: *Jan. 9, 2024

(54) COMPOSITIONS OF TROFINETIDE

(71) Applicant: NEUREN PHARMACEUTICALS LIMITED, Auckland (NZ)

(72) Inventors: Clive Blower, Doncaster East (AU); Mathew Peterson, San Diego, CA (US); James Murray Shaw, Parkdale (AU); James Anthony Bonnar, Ryde (AU); Etienne David Frank Philippe Moniotte, Waterloo (BE); Martin Bernard Catherine Bousmanne, Woluwe Saint-Labmert (BE); Cecilia Betti, Brussels (BE); Karel Willy Luc Decroos, Ghent (BE); Mimoun Ayoub, Staefa (CH)

(73) Assignee: NEUREN PHARMACEUTICALS LIMITED, Auckland (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 17/847,736

(22) Filed: Jun. 23, 2022

(65) Prior Publication Data

US 2022/0324799 A1 Oct. 13, 2022

Related U.S. Application Data

(63) Continuation of application No. 17/347,135, filed on Jun. 14, 2021, now Pat. No. 11,370,755, which is a continuation of application No. PCT/US2020/044733, filed on Aug. 3, 2020.

(60) Provisional application No. 62/882,998, filed on Aug. 5, 2019.

(51) Int. Cl.
| | |
|---|---|
| *C07D 207/16* | (2006.01) |
| *B01J 21/06* | (2006.01) |
| *B01J 21/18* | (2006.01) |
| *B01J 23/44* | (2006.01) |

(52) U.S. Cl.
CPC ............ *C07D 207/16* (2013.01); *B01J 21/06* (2013.01); *B01J 21/18* (2013.01); *B01J 23/44* (2013.01); *C07B 2200/07* (2013.01)

(58) Field of Classification Search
CPC ......... C07D 207/16; B01J 21/06; B01J 21/18; B01J 23/44; C07B 2200/07; A61K 38/06; C07K 5/0806; A61P 25/28
USPC ....................................................... 514/359
See application file for complete search history.

(56) References Cited

U.S. PATENT DOCUMENTS

| | | | |
|---|---|---|---|
| 4,725,645 A | 2/1988 | Anteunis et al. | |
| 7,041,314 B2 | 5/2006 | Abood et al. | |
| 7,605,177 B2 | 10/2009 | Gluckman et al. | |
| 7,714,020 B2 | 5/2010 | Gluckman et al. | |
| 7,863,304 B2 | 1/2011 | Brimble et al. | |
| 7,887,839 B2 | 2/2011 | Wen et al. | |
| 8,178,125 B2 | 5/2012 | Wen et al. | |
| 8,496,963 B2 | 7/2013 | Wen et al. | |
| 8,546,530 B2 | 10/2013 | Cellens et al. | |
| 8,637,567 B2 | 1/2014 | Gluckman et al. | |
| 9,212,204 B2 | 12/2015 | Glass et al. | |
| 9,708,366 B2 | 7/2017 | Glass et al. | |
| 11,370,755 B2 * | 6/2022 | Blower | B01J 21/18 |
| 2009/0074865 A1 | 3/2009 | Wen et al. | |
| 2014/0147491 A1 | 5/2014 | Glass et al. | |

FOREIGN PATENT DOCUMENTS

WO WO-2021026066 A1 2/2021

OTHER PUBLICATIONS

Cacciatore, I., et al., "Development of glycine-α-methyl-proline-containing tripeptides with neuroprotective properties," *European Journal of Medicinal Chemistry* 108:553-563, Elsevier, Netherlands (Jan. 2016).
Harris, P., et al., "Synthesis of proline-modified analogues of the neuroprotective agent glycyl-l-prolyl-glutamic acid (GPE)," *Tetrahedron* 67:10018-10035, Elsevier, Netherlands (Oct. 2005).
Pubmed Compound Record for CID 67171960, "(2S)-2-[[(2S)-2-Methyl-1-[2-(phenylmethoxycarbonylamino )acetyl]pyrrolidine-2-carbonyl]amino]pentanedioicacid", U.S. National Library of Medicine, created Nov. 30, 2012, accessed at https://pubchem.ncbi.nlm.nih.gov/compound/67171960, 10 pages.

(Continued)

*Primary Examiner* — Taylor V Oh
(74) *Attorney, Agent, or Firm* — Sterne, Kessler, Goldstein & Fox P.L.L.C.

(57) ABSTRACT

This disclosure describes compounds of Formula (I), stereoisomers, side compounds thereof, pharmaceutical compositions and methods of manufacturing such compounds, using silylation reagents and producing compositions and products made using such methods. More particularly, this disclosure describes manufacture of trofinetide and side products, compositions and products containing such compounds, for pharmaceutical uses to treat neurodegenerative or neurodevelopmental disorders.

(I)

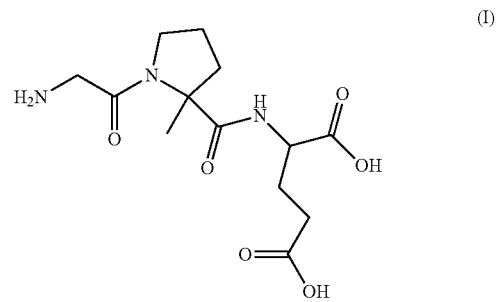

20 Claims, No Drawings

(56) References Cited

OTHER PUBLICATIONS

International Search Report for International Application No. PCT/US2020/044733, USPTO, dated Dec. 7, 2020.
Written Opinion of the International Searching Authority for International Application No. PCT/US2020/044733, USPTO, dated Dec. 7, 2020.
Rogozhin. S. V., et al., "Preparation of trimethylsilyl derivatives of amino acids and peptides for peptide synthesis," *Bulletin of the Academy of Sciences of the USSR, Division of chemical science* 23: 1789-1792, Plenum Publishing Corporation, New York (1974).

* cited by examiner

COMPOSITIONS OF TROFINETIDE

FIELD OF THE DISCLOSURE

This disclosure provides for compositions and methods of manufacture containing trofinetide (Glycyl-L-2-Methylprolyl-L-Glutamic acid, or "G-2-MePE"). Compositions are made using new manufacturing methods and contain trofinetide and other products of the synthetic methods.

BACKGROUND

Trofinetide is a synthetic compound, having a similar core structure to Glycyl-Prolyl-Glutamic acid (or "GPE"). Trofinetide has been found to be useful in treating neurodegenerative conditions and recently has been found to be effective in treating Autism Spectrum disorders and Neurodevelopmental disorders.

SUMMARY

The inventors have identified a new problem in the field, namely that current methods of producing compositions containing trofinetide are difficult to scale to commercial quantities.

To address this problem, we have identified new compositions and manufacturing methods in which the compound or salt or stereoisomer or hydrate thereof is made using silylation technology. Use of this new strategy provides for new compositions and substantially larger quantities of trofinetide to be produced, and results in compositions, kits, and products containing trofinetide that are commercially beneficial.

This disclosure includes a composition comprising a compound of Formula (I)

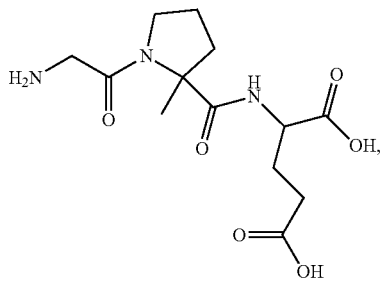

(I)

or a stereoisomer, hydrate, or pharmaceutically acceptable salt thereof, and a compound of Formula (II):

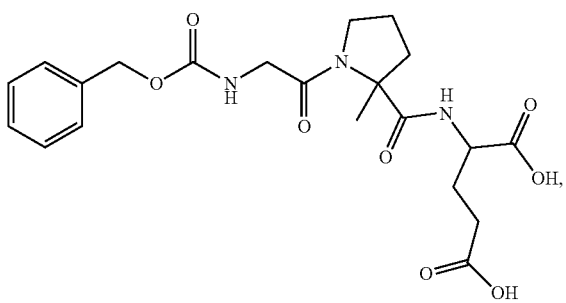

(II)

or a stereoisomer, hydrate, or pharmaceutically acceptable salt thereof, and/or a compound of Formula (III):

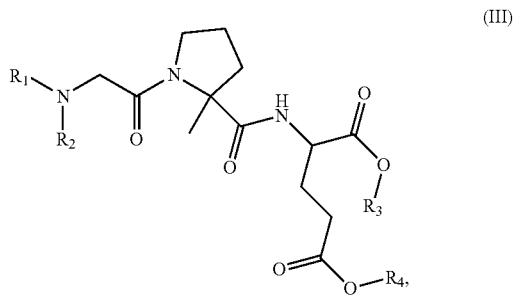

(III)

or a stereoisomer, hydrate, or pharmaceutically acceptable salt thereof, wherein $R_1$, $R_2$, $R_3$ and $R_4$ independently are selected from the group consisting of hydrogen and $C_{1-4}$ alkyl, provided that least one of $R_1$, $R_2$, $R_3$ and $R_4$ is $C_{1-4}$ alkyl.

This disclosure also includes a compound according to Formula (Ia) (trofinetide)

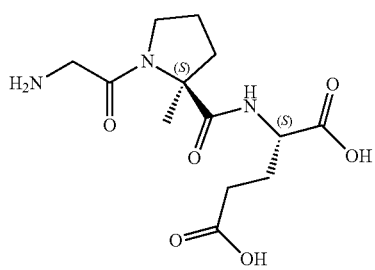

or a hydrate, or pharmaceutically acceptable salt thereof.

This disclosure also includes a composition comprising trofinetide, said composition obtained by:

a) coupling H-MePro-OH and Z-Gly-OH in the presence of an activating reagent, silylating agent and a solvent, or b) coupling Z-Gly-OH and Suc-OH and then coupling the obtained Z-Gly-OSu and H-MePro-OH in the absence or presence of an activating reagent, a solvent and in the absence or presence of a silylating agent;

c) coupling the obtained Z-Gly-MePro-OH and H-Glu-OH in the presence of an activating reagent, silylating agent and a solvent;

d) obtaining Z-Gly-MePro-Glu-OH; and e) deprotecting Z-Gly-MePro-Glu-OH, to obtain a composition comprising trofinetide.

This disclosure also includes a method of manufacturing a composition containing trofinetide comprising the steps:

a) coupling H-MePro-OH and Z-Gly-OH in the presence of an activating reagent, silylating agent and a solvent, or b) coupling Z-Gly-OH and Suc-OH and then coupling the obtained Z-Gly-OSu and H-MePro-OH in the absence or presence of an activating reagent, a solvent and in the absence or presence of a silylating agent;

c) coupling the obtained Z-Gly-MePro-OH and H-Glu-OH in the presence of an activating reagent, silylating agent and a solvent;

d) obtaining Z-Gly-MePro-Glu-OH; and e) deprotecting Z-Gly-MePro-Glu-OH, to obtain a composition comprising trofinetide.

This disclosure also includes a kit containing a dosage form comprising a compound of trofinetide and a compound of Formula (IIa),

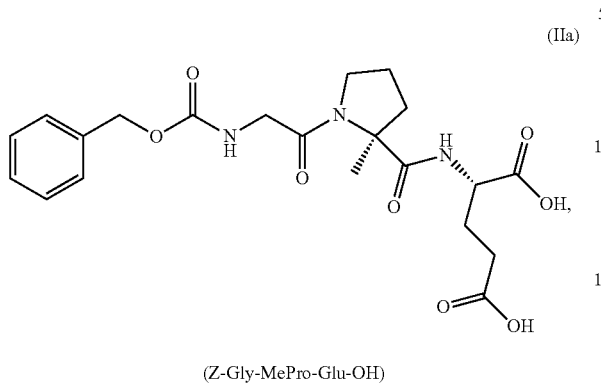

(Z-Gly-MePro-Glu-OH)

or a hydrate, or pharmaceutically acceptable salt thereof, and instructions for use.

This disclosure also includes a kit containing a dosage form comprising a compound of Formula (Ia) and a compound of Formula (IIa), and one or more compounds selected from the group consisting of Formula (III), Formula (IIIa), Formula (IV), Formula (V), Formula (VI), Formula (VII), Formula (VIII), and Formula (IX).

DETAILED DESCRIPTION

Synthesis of peptides using persilylation generally involves selection of a peptide or amino acid, followed by several steps. In a first step, the peptide or amino acid is reacted with a persilylating agent, optionally in an organic solvent. It can be desirable to use persilylating agents selected from the group consisting of N,O-bis(trimethylsilyl)acetamide (BSA), N,O-bis(trimethylsilyl)trifluoroacetamide, hexamethyldisilazane, N-methyl-N-(trimethylsilyl)acetamide (TMA), N.-methyl-N-(trimethylsilyl)trifluoroacetamide, N-(trimethylsilyl)acetamide, N-(trimethylsilyl)diethylamine, N-(trimethylsilyl)dimethylamine, 1-(trimethylsilyl)imidazole, and 3-(trimethylsilyl)2-oxazolidone.

Utility

Trofinetide has been shown to be useful in treating neurodegenerative conditions, neurodevelopmental disorders and autism spectrum disorders.

Definitions

The following definitions are to be understood as stated unless they are specifically defined elsewhere in this disclosure.

The term "Cbz" and "Z" mean a benzyloxycarbonyl protecting group, and are interchangeable with each other and has the following structure:

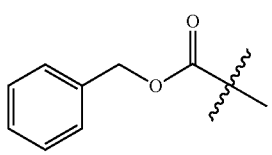 [SMILES: *C(=O)OCc1ccccc1]

The term "trofinetide" means glycyl-L-2-methylprolyl-L-glutamic acid of Formula (Ia) or "G-2-MePE", or "H-Gly-MePro-Glu-OH", or "Gly-MePro-Glu-OH" wherein the chiral centers are in S,S configuration

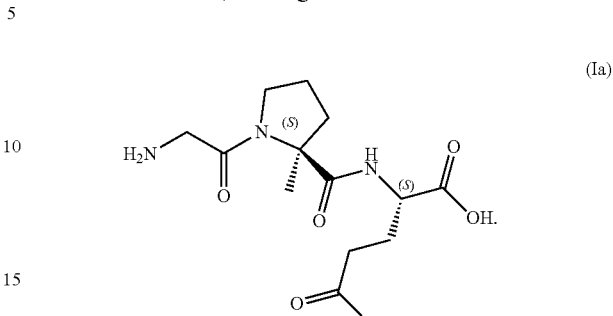

The IUPAC name of trofinetide is (2S)-[[(2S)-1-(2-aminoace)-2-methylpyrrolidine-2-carbonyl]amino]pentanedioic acid The term "about" means the average value of a variable ±20% of the average value of the variable.

The term "eq" means "equivalent". Unless specified otherwise, all equivalents (eq) are expressed with respect to the limiting reagent on a mole basis.

The terms "vol" and "vols" mean "volume" and "volumes" respectively.

The term "DIPEA" means N,N-diisopropylethylamine, or Hünig's base.

The term "DMAC" means N,N-dimethylacetamide.

The term "NMT" means "not more than".

The term "TMA" means N-methyl-N-(trimethylsilyl)acetamide.

The term "BSA" means N,O-bis(trimethylsilyl)acetamide.

The term "Oxyma Pure" means ethyl 2-cyano-2-(hydroxyimino)acetate, or ethyl(hydroxyimino)cyanoacetate.

The term "IPE" means iso-propyl ether or diisopropyl ether.

The term "ACN" means acetonitrile.

The term "NLT" means "not less than".

The term "MTBE" means 2-methoxy-2-methylpropane, or methyl-tert-butyl ether.

The term "iPrOH" means propan-2-ol, or isopropyl alcohol, or isopropanol.

The term "iPrOAc" means isopropyl acetate.

The term "UPLC" means ultra-performance liquid chromatography.

The term "Piv-Cl" means pivaloyl chloride.

The term "EtOAc" or "AcOEt" means ethyl acetate.

The term "HPLC" means high-performance liquid chromatography.

The term "MeOH" means methyl alcohol or methanol.

The term "Pd/C" means a palladium on carbon catalyst.

The term "Pd/Si" means a palladium on silica catalyst.

The term "RT" means surrounding temperature, generally about 25° C.

The term "LC" means liquid chromatography.

The term "RRT" means relative retention time.

The term "TFA" means trifluoroacetic acid.

The term "H-MePro-OH" means (2S)-2-methylpyrrolidine-2-carboxylic acid in either the base or hydrochloride salt form.

The term "MePro·HCl" means (2S)-2-methylpyrrolidine-2-carboxylic acid hydrochloride.

The term "Z-Gly-OH" means benzyloxycarbonyl-glycine, or Cbz-glycine.

The term "H-Glu-OH" means (2S)-2-aminopentanedioic acid, or L-glutamic acid.

The term "EDC·HCl" means 1-(3-dimethylaminopropyl)-3-ethylcarbodiimide hydrochloride, or 1-ethyl-3-(3-dimethylaminopropyl)carbodiimide hydrochloride, or N-(3-dimethylaminopropyl)-N'-ethylcarbodiimide hydrochloride.

The term "Z-Gly-MePro-OH" means ((S)-1-(((benzyloxy)carbonyl)glycyl)-2-methylpyrrolidine-2-carboxylic acid), or N-benzyloxycarbonyl-glycyl-L-2-methylproline.

The term "Z-Gly-MePro-Glu-OH" means ((S)-1-(((benzyloxy)carbonyl)glycyl)-2-methylpyrrolidine-2-carbonyl)-L-glutamic acid, or N-benzyloxycarbonyl-glycyl-L-2-methylprolyl-L-glutamic acid.

The term "Et-Gly-MePro-Glu-OH" means ((S)-1-(ethylglycyl)-2-methylpyrrolidine 2-carbonyl)-L-glutamic acid, or N-ethyl-glycyl-L-2-methylprolyl-L-glutamic acid.

The term "Me-Gly-MePro-Glu-OH" means ((S)-1-(methylglycyl)-2-methylpyrrolidine-2-carbonyl)-L-glutamic acid, or methyl-glycyl-L-2-methylprolyl-L-glutamic acid.

The term "Me$_2$-Gly-MePro-Glu-OH" means ((S)-1-(dimethylglycyl)-2-methylpyrrolidine-2-carbonyl)-L-glutamic acid, or N,N-dimethyl-glycyl-L-2-methylprolyl-L-glutamic acid.

The term "Gly-MePro-Glu(OiPr)-OH" means glycyl-L-2-methylprolyl-L-glutamic acid 5-isopropyl ester, or glycyl-L-2-methylprolyl-L-glutamic γ isopropyl ester.

The term "Gly-MePro-Glu-OiPr" means glycyl-L-2-methylprolyl-L-glutamic acid 1-isopropyl ester, or glycyl-L-2-methylprolyl-L-glutamic α isopropyl ester.

The term "Gly-MePro-Glu(OiPr)-OiPr" means glycyl-L-2-methylprolyl-Lglutamic acid 1,5-diisopropyl ester.

The term "Gly-MePro-Glu(OMe)-OH" means glycyl-L-2-methylprolyl-L-glutamic acid 5-methyl ester, or glycyl-L-2-methylprolyl-L-glutamic γ methyl ester.

The term "Gly-MePro-Glu-OMe" means glycyl-L-2-methylprolyl-L-glutamic acid 1-methyl ester, or glycyl-L-2-methylprolyl-L-glutamic α methyl ester.

The term "Gly-MePro-Glu(OMe)-OMe" means glycyl-L-2-methylprolyl-L-glutamic acid 1,5-dimethyl ester.

The term "Gly-MePro-Glu(OEt)-OH" means glycyl-L-2-methylprolyl-L-glutamic acid 5-ethyl ester, or glycyl-L-2-methylprolyl-L-glutamic γ ethyl ester.

The term "Gly-MePro-Glu-OEt" means glycyl-L-2-methylprolyl-L-glutamic acid 1-ethyl ester, or glycyl-L-2-methylprolyl-L-glutamic α ethyl ester.

The term "Gly-MePro-Glu(OEt)-OEt" means glycyl-L-2-methylprolyl-L-glutamic acid 1,5-diethyl ester.

The term "Suc-OH" means N-hydroxysuccinimide

The term "Z-Gly-OSu" means benzyloxycarbonyl-glycine N-succinimidyl ester.

The term "DCC" means N,N'-dicyclohexylcarbodiimide.

The term "DCU" means 1,3-dicyclohexyl urea.

The term "TEA" means triethylamine

The term "CH$_2$Cl$_2$" means DCM, or dichloromethane.

The term "NaHCO$_3$" means sodium bicarbonate.

The term "iButOH" means butan-2-ol, or isobutyl alcohol, or isobutanol.

The term "DMAPA" means dimethylaminopropylamine

The term "KHSO$_4$" means potassium bisulfate.

The term "H$_2$O" means water.

The term "NaCl" means sodium chloride, or salt.

The term "DMA" means N,N-dimethylacetamide.

The term "DMF" means N,N-dimethylformamide

The term "HCl" means hydrochloric acid.

The term "HOBt" means 1-hydroxy-benzotriazole.

The term "HOAt" means 1-hydroxy-azabenzotriazole.

The term "TBTU" means 2-(1H-benzotriazole-1-yl)-1,1,3,3-tetramethylaminium tetrafluoroborate.

The term "NMM" means N-methylmorpholine.

The term "ICH" means the International Council for Harmonisation

The term "NMR" means nuclear magnetic resonance.

The term "UV" means ultra-violet.

The term "MS" means mass spectrometry.

The term "gm" means gram.

The term "μl" means microliter.

The terms "activating reagent" and "carboxyl group activating reagent" means a reagent that facilitates the coupling of two amino acids and/or peptides by formation of an amide bond. Examples of activating agents and carboxyl group activating agents include carbodiimides, acyl halides, phosphonium salts and uronium or guanidinium salts, acyl halides, such as isobutyl chloroformate or pivaloyl chloride or a carbodiimide, such as EDC·HCl or DCC.

The term "comprising" means includes but not limited to.

The term "consisting of" means includes only the stated material.

The term "consisting essentially of" means includes the stated material and equivalents thereof.

The terms "% w/w" and "wt %" are used interchangeably throughout the present disclosure.

The term "specified amount" means the amount of compound expressed in units of mass/volume or mass/mass that is intended to be present in a product. The actual amount of a compound can exceed 100 wt % of the specified amount if it contains an overage to compensate for compound loss on storage, for example, by breakdown or degradation of the compound.

The term "persilyating agent" or "silylating agent" means a compound that adds silicon atoms to a peptide or amino acid.

The term "persilylated" denotes a compound in which the groups having an active hydrogen atom that can react with the silylating agent are sufficiently silylated to ensure that a homogeneous reaction medium is obtained.

The term "functional groups to be silylated" is understood to denote in particular groups having an active hydrogen atom that react with the silylating agent such as amino, hydroxyl, mercapto or carboxyl groups.

The term "side product(s)" means compounds of Formulae (II), (IIa), (III), (IIIa), (IV), (V), (VI), (VII), (VIII), and (IX).

General Description

This disclosure includes descriptions of methods of manufacture of compounds of Formula (I), compounds and compositions including compounds of Formula (I) and compounds of Formula (II), and/or Formula (III), and/or Formula (IV), and/or Formula (V), and/or Formula (VI), and/or Formula (VII), and/or Formula (VIII), and/or Formula (IX), and products containing compositions containing one or more compounds of these formulae. The general approach disclosed involves synthesis of compounds using silylating agents. Based on the chirality of the starting materials, mixtures of compounds can be produced, with the majority of compounds having chirality of the starting materials, and some additional compounds having different chiralities.

These compounds and compositions are useful in treating a variety of neurodegenerative disorders, autism spectrum disorders, and neurodevelopmental disorders.

Compounds of this Disclosure

The following compounds are to be considered independent of each other, but can be combined with any other compounds. They include compounds of Formula (I), and compounds of Formulae (II), (IIa), (III), (IIIa), (IV), (V), (VI), (VII), (VIII), and (IX).

A compound of Formula (I)

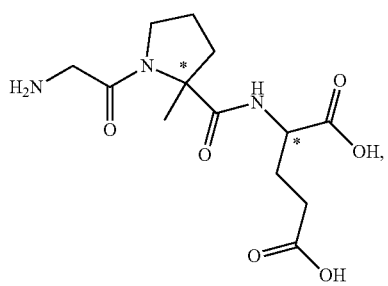

(I)

or hydrate, or pharmaceutically acceptable salt thereof wherein the chiral centers are either S,S, S,R, R,S, or R,R configurations, and wherein the chiral center is denoted with * in Formula (I). Chiral centers for Formulae (Ia), (II), (IIa), (III), (IIIa), (IV), (V), (VI), (VII), (VIII), and (IX) are the same as for Formula (I).

A compound of Formula (Ia)

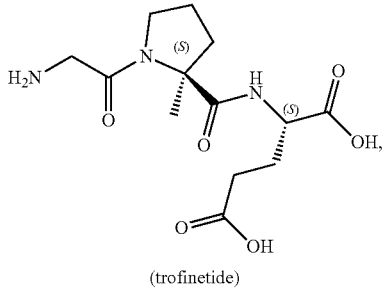

(Ia)

(trofinetide)

or hydrate, or pharmaceutically acceptable salt thereof wherein the chiral centers are in S,S configurations.

A compound of Formula (II)

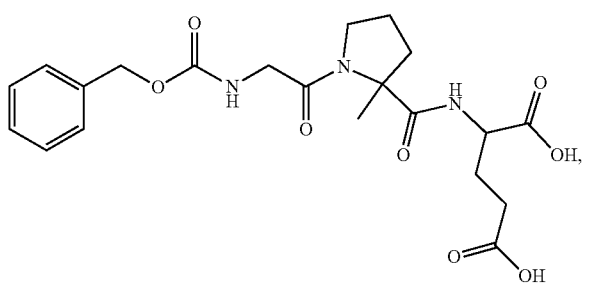

(II)

or hydrate, or pharmaceutically acceptable salt thereof wherein the chiral centers are either S,S, S,R, R,S, or R,R configurations.

A compound of Formula (IIa)

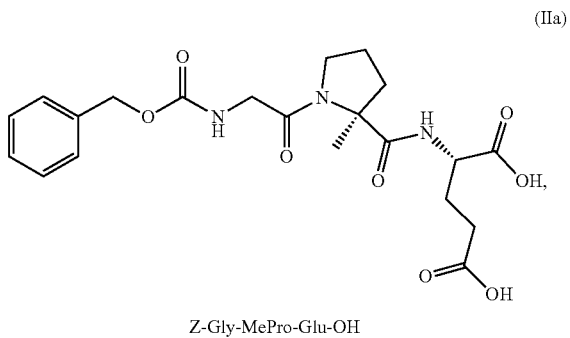 [SMILES: C[C@@]1(C(=O)N[C@@H](CCC(=O)O)C(=O)O)CCCN1C(=O)CNC(=O)OCc1ccccc1]

(IIa)

Z-Gly-MePro-Glu-OH or hydrate, or pharmaceutically acceptable salt thereof wherein the chiral centers are in S,S configurations.

A compound of Formula (III)

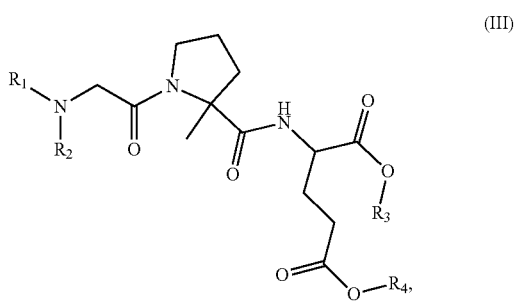

(III)

or hydrate, or pharmaceutically acceptable salt thereof wherein the chiral centers are either S,S, S,R, R,S, or R,R configurations, and wherein $R_1$, $R_2$, $R_3$ and $R_4$ independently are selected from the group consisting of hydrogen and $C_{1-4}$ alkyl, provided that least one of $R_1$, $R_2$, $R_3$ and $R_4$ is $C_{1-4}$ alkyl.

A compound of Formula (III), comprising Gly-MePro-Glu(OMe)-OH, meaning glycyl-L-2-methylprolyl-L-glutamic acid 5-methyl ester, or glycyl-L-2-methylprolyl-L-glutamic γ methyl ester.

A compound of Formula (III), comprising Gly-MePro-Glu-OMe meaning glycyl-L-2-methylprolyl-L-glutamic acid 1-methyl ester, or glycyl-L-2-methylprolyl-L-glutamic α methyl ester.

A compound of Formula (III), comprising Gly-MePro-Glu(OMe)-OMe meaning glycyl-L-2-methylprolyl-L-glutamic acid 1,5-dimethyl ester.

A compound of Formula (III), comprising Gly-MePro-Glu(OEt)-OH meaning glycyl-L-2-methylprolyl-L-glutamic acid 5-ethyl ester, or glycyl-L-2-methylprolyl-L-glutamic γ ethyl ester.

A compound of Formula (III), comprising Gly-MePro-Glu-OEt meaning glycyl-L-2-methylprolyl-L-glutamic acid 1-ethyl ester, or glycyl-L-2-methylprolyl-L-glutamic α ethyl ester.

A compound of Formula (III), comprising Gly-MePro-Glu(OEt)-OEt meaning glycyl-L-2-methylprolyl-L-glutamic acid 1,5-diethyl ester.

A compound of Formula (IIIa)

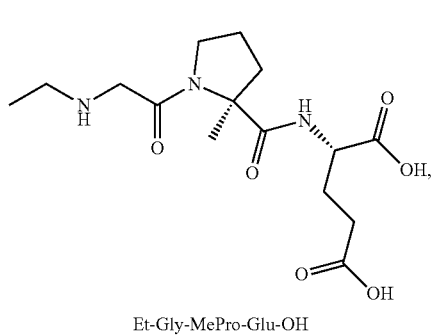

Et-Gly-MePro-Glu-OH or hydrate, or pharmaceutically acceptable salt thereof wherein the chiral centers are in S,S configurations.

A compound of Formula (IV)

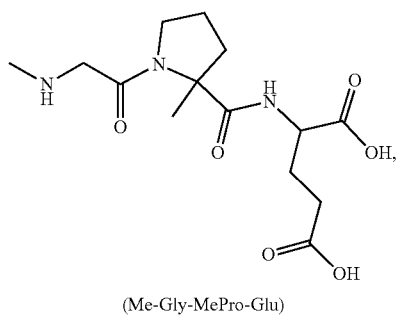

(Me-Gly-MePro-Glu)

or hydrate, or pharmaceutically acceptable salt thereof wherein the chiral centers are either S,S, S,R, R,S, or R,R configurations.

A compound of Formula (V)

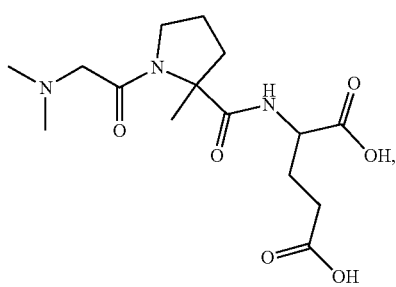

(Me$_2$-Gly-MePro-Glu)

or hydrate, or pharmaceutically acceptable salt thereof wherein the chiral centers are either S,S, S,R, R,S, or R,R configurations.

A compound of Formula (VI)

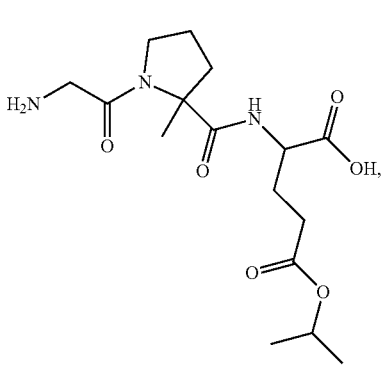

(Gly-MePro-Glu(OiPr)-OH)

or hydrate, or pharmaceutically acceptable salt thereof wherein the chiral centers are either S,S, S,R, R,S, or R,R configurations.

A compound of Formula (VII)

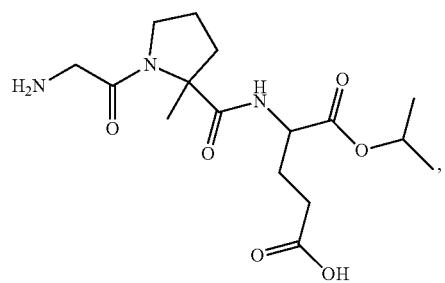

(Gly-MePro-Glu-OiPr)

or hydrate, or pharmaceutically acceptable salt thereof wherein the chiral centers are either S,S, S,R, R,S, or R,R configurations.

A compound of Formula (VIII)

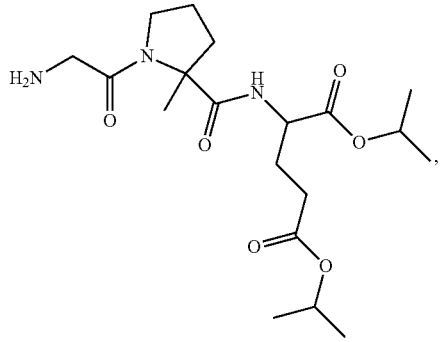

(Gly-MePro-Glu-(OiPr)$_2$)

or hydrate, or pharmaceutically acceptable salt thereof wherein the chiral centers are either S,S, S,R, R,S, or R,R configurations.

A compound of Formula (IX)

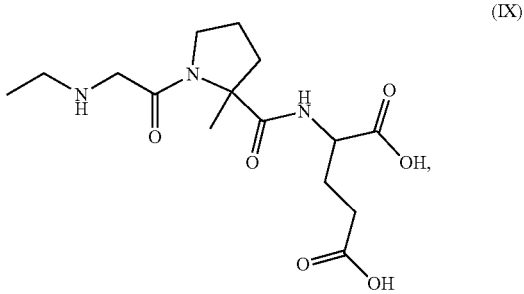 [SMILES: CCNCC(=O)N1CCCC1(C)C(=O)NC(CCC(=O)O)C(=O)O]

or hydrate, or pharmaceutically acceptable salt thereof wherein the chiral centers are either S,S, S,R, R,S, or R,R configurations.

Compounds of Formulae (II), (IIa), (III), (IIIa), (IV), (V), (VI), (VII), (VIII), and (IX) whenever present are side products in the compositions disclosed herein.

Compositions, Manufacture, and Products of this Disclosure

Products of this disclosure refer to un-isolated materials, isolated materials, chemical intermediates, formulations, dosage forms, kits, instructions, and the like for use that contain compositions of this disclosure. The compositions and products of this disclosure include the following:

A composition comprising a compound of Formula (I), a stereoisomer, hydrate, or pharmaceutically acceptable salt thereof, and a compound of Formula (II), a stereoisomer, hydrate, or pharmaceutically acceptable salt thereof.

A composition comprising a compound of Formula (I), a stereoisomer, hydrate, or pharmaceutically acceptable salt, and a compound of Formula (II), a stereoisomer, hydrate, or pharmaceutically acceptable salt thereof, and/or a compound of Formula (III), a stereoisomer, hydrate, or pharmaceutically acceptable salt thereof.

A composition comprising a compound of Formula (I), a stereoisomer, hydrate, or pharmaceutically acceptable salt, and a compound of Formula (II), a stereoisomer, hydrate, or pharmaceutically acceptable salt, and/or a compound of Formula (IX), a stereoisomer, hydrate, or pharmaceutically acceptable salt.

A composition comprising a compound of Formula (Ia) (trofinetide), a hydrate, or pharmaceutically acceptable salt thereof and at least a compound of Formula (IIa), hydrate, or pharmaceutically acceptable salt thereof.

A composition comprising a compound of Formula (Ia) (trofinetide) and a compound of Formula (IIa).

A composition comprising a compound of Formula (Ia) (trofinetide), a hydrate, or pharmaceutically acceptable salt thereof, and a compound of Formula (IIa), a hydrate, or pharmaceutically acceptable salt thereof, and/or a compound of Formula (IIIa), a hydrate, or pharmaceutically acceptable salt thereof.

A composition comprising a compound of Formula (Ia) (trofinetide), a hydrate, or pharmaceutically acceptable salt thereof and a compound of Formula (IIa), a hydrate, or pharmaceutically acceptable salt thereof and/or a compound of Formula (III), a hydrate, or pharmaceutically acceptable salt thereof.

A composition comprising a compound of Formula (Ia) (trofinetide) and a compound of Formula (II) and/or a compound of Formula (III).

A composition comprising a compound of Formula (I), a stereoisomer, hydrate, or pharmaceutically acceptable salt thereof, and a compound of Formula (II), a stereoisomer, hydrate, or pharmaceutically acceptable salt thereof, and/or a compound of Formula (IV), a stereoisomer, hydrate, or pharmaceutically acceptable salt thereof.

A composition comprising a compound of Formula (I), a stereoisomer, hydrate, or pharmaceutically acceptable salt thereof, and a compound of Formula (II), a stereoisomer, hydrate, or pharmaceutically acceptable salt thereof, and/or a compound of Formula (V), a stereoisomer, hydrate, or pharmaceutically acceptable salt thereof.

A composition comprising a compound of Formula (I), a stereoisomer, hydrate, or pharmaceutically acceptable salt thereof, and a compound of Formula (II), a stereoisomer, hydrate, or pharmaceutically acceptable salt thereof, and/or a compound of Formula (VI), a stereoisomer, hydrate, or pharmaceutically acceptable salt thereof.

A composition comprising a compound of Formula (I), a stereoisomer, hydrate, or pharmaceutically acceptable salt thereof, and a compound of Formula (II), a stereoisomer, hydrate, or pharmaceutically acceptable salt thereof, and/or a compound of Formula (VII), a stereoisomer, hydrate, or pharmaceutically acceptable salt thereof.

A composition comprising a compound of Formula (I), a stereoisomer, hydrate, or pharmaceutically acceptable salt thereof, and a compound of Formula (II), a stereoisomer, hydrate, or pharmaceutically acceptable salt thereof, and/or a compound of Formula (VIII), a stereoisomer, hydrate, or pharmaceutically acceptable salt thereof.

A composition comprising a compound of Formula (I), a stereoisomer, hydrate or pharmaceutically acceptable salt thereof, and a compound of Formula (III).

A composition comprising a compound of Formula (Ia), a hydrate or pharmaceutically acceptable salt thereof, and a compound of Formula (IIIa).

A kit containing a dosage form comprising a compound of Formula (Ia) (trofinetide) and a compound of Formula (IIa) and instructions for use.

A kit may additionally comprise one or more compounds selected from the group consisting of Formula (III), Formula (IIIa), Formula (IV), Formula (V), Formula (VI), Formula (VII), Formula (VIII), and Formula (IX).

Embodiments

A composition of any following embodiment, comprising a compound of Formula (I)

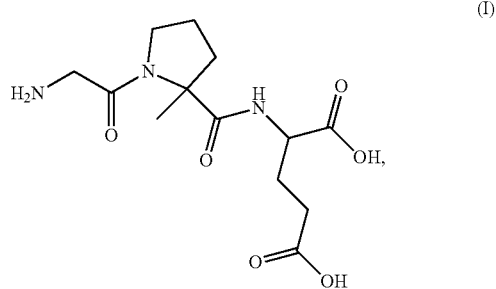 [SMILES: CC1(C(=O)NC(CCC(=O)O)C(=O)O)CCCN1C(=O)CN]

or a stereoisomer, hydrate, or pharmaceutically acceptable salt thereof, and a compound of Formula (II):

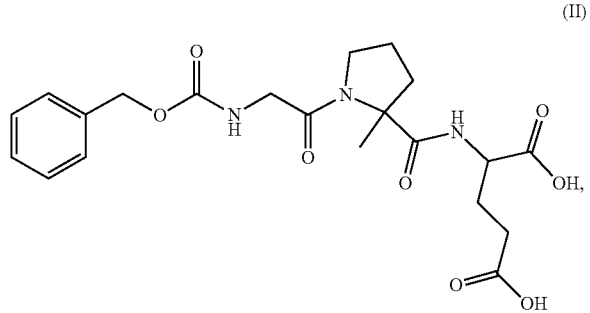 [SMILES: CC1(C(=O)NC(CCC(=O)O)C(=O)O)CCCN1C(=O)CNC(=O)OCc1ccccc1]

(II)

or a stereoisomer, hydrate, or pharmaceutically acceptable salt thereof, and/or a compound of Formula (III):

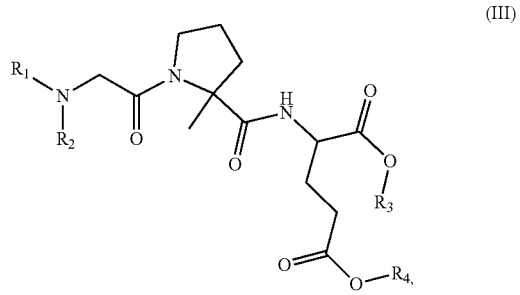

(III)

or a stereoisomer, hydrate, or pharmaceutically acceptable salt thereof, wherein $R_1$, $R_2$, $R_3$ and $R_4$ independently are selected from the group consisting of hydrogen and $C_{1-4}$ alkyl, provided that least one of $R_1$, $R_2$, $R_3$ and $R_4$ is $C_{1-4}$ alkyl.

The composition according to any preceding or following embodiment, wherein the compound according to Formula (I) is a compound of Formula (Ia).

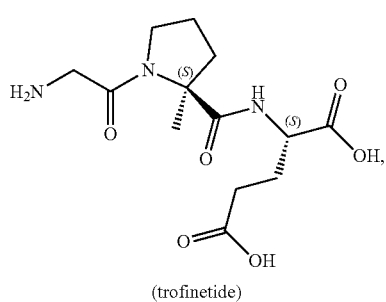

(Ia)

(trofinetide)

or a hydrate, or pharmaceutically acceptable salt thereof.

The composition of any preceding or following embodiment, wherein the compound of Formula (II), or stereoisomer, hydrate, or pharmaceutically acceptable salt thereof, is absent or present in an amount between about 0.001±0.0002 wt % and about 2±0.4 wt %; and the compound of Formula (III), or stereoisomer, hydrate, or pharmaceutically acceptable salt thereof, is absent or present in an amount between about 0.001±0.0002 wt % and about 2±0.4 wt %, provided that at least one of the compounds of Formula (II) or (III), or stereoisomer, hydrate, or pharmaceutically acceptable salt thereof, is present.

The composition according to any preceding or following embodiment, wherein the compound of Formula (II), or stereoisomer, hydrate, or pharmaceutically acceptable salt thereof, is present in an amount of between about 0.001±0.0002 wt % and about 0.3±0.06 wt %.

The composition according to any preceding or following embodiment, wherein the compound of Formula (II), or stereoisomer, hydrate, or pharmaceutically acceptable salt thereof, is present in an amount between about 0.001±0.0002 wt % and about 0.1±0.02 wt %.

The composition according to any preceding or following embodiment, wherein the compound of Formula (II), or stereoisomer, hydrate, or pharmaceutically acceptable salt thereof, is present in an amount between about 0.001±0.0002 wt % and about 2±0.4 wt %, or between about 0.001±0.0002 wt % and about 1.5±0.3 wt %, or between about 0.001±0.0002 wt % and about 1±0.2 wt %, or between about 0.001±0.0002 wt % and about 0.7±0.14 wt %, or between about 0.001±0.0002 wt % and about 0.5±0.1 wt %, or between about 0.001±0.0002 wt % and about 0.3±0.06 wt %, or between about 0.001±0.0002 wt % and about 0.2±0.04 wt %.

The composition according to any preceding or following embodiment, wherein the compound according to Formula (II) is a compound of Formula (IIa):

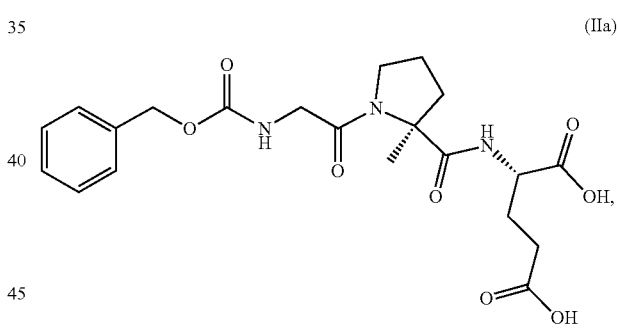

(IIa)

(Z-Gly-MePro-Glu-OH)

or a hydrate, or pharmaceutically acceptable salt thereof.

The composition according to any preceding or following embodiment, wherein the compound of Formula (II), or stereoisomer, hydrate, or pharmaceutically acceptable salt thereof, is absent.

The composition according to any preceding or following embodiment, wherein the compound of Formula (III), or stereoisomer, hydrate, or pharmaceutically acceptable salt thereof, is present in an amount between about 0.001±0.0002 wt % and about 2.0±0.4 wt %.

The composition according to any preceding or following embodiment, wherein said composition comprising the compound of Formula (III), wherein the compound of Formula (III) is a compound of Formula (IX),

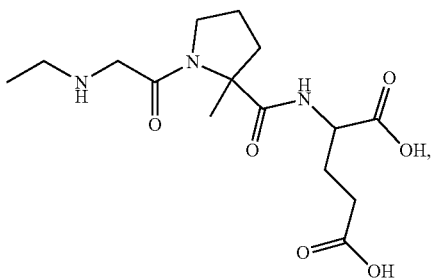

or hydrate, or pharmaceutically acceptable salt thereof.

The composition according to any preceding or following embodiment, comprising the compound of Formula (III), wherein the compound according to Formula (III) is a compound of Formula (IIIa):

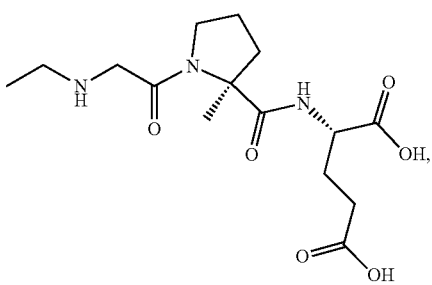

(Et-Gly-MePro-Glu-OH)

or hydrate, or pharmaceutically acceptable salt thereof.

The composition according to any preceding or following embodiment, wherein the compound of Formula (IIIa), or hydrate, or pharmaceutically acceptable salt thereof, is present in an amount between about 0.001±0.0002 wt % and about 2.0±0.4 wt %.

The composition according to any preceding or following embodiment, wherein the compound of Formula (IIIa), or hydrate, or pharmaceutically acceptable salt thereof is present in an amount between about 0.001±0.0002 wt % and about 2.0±0.4 wt %, or between about 0.001±0.0002 wt % and about 1.5±0.3 wt %, or between about 0.001±0.0002 wt % and about 1±0.2 wt %, or between about 0.001±0.0002 wt % and about 0.7±0.14 wt %, or between about 0.001±0.0002 wt % and about 0.5±0.1 wt %, or between about 0.001±0.0002 wt % and about 0.3±0.06 wt %, or between about 0.001±0.0002 wt % and about 0.2±0.04 wt %.

The composition according to any preceding or following embodiment comprising between about 97 wt % and about 100 wt % of the compound of Formula (Ia), alternatively between about 98 wt % and 100 wt %, or between about 99 wt % and 100 wt % on an anhydrous basis.

The composition according to any preceding or following embodiment, wherein the compound according to Formula (III) is a compound of Formula (IV):

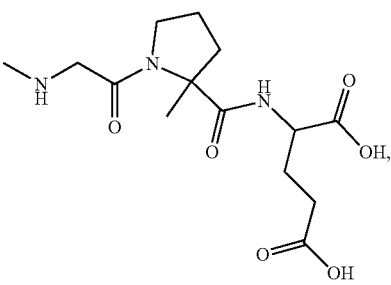

(Me-Gly-MePro-Glu)

Or a stereoisomer, hydrate, or pharmaceutically acceptable salt thereof.

The composition according to any preceding or following embodiment, wherein the compound of Formula (IV), or stereoisomer, hydrate, or pharmaceutically acceptable salt thereof, is present in an amount between about 0.001±0.0002 wt % and about 2±0.4 wt %, or between about 0.001±0.0002 wt % and about 1.5±0.3 wt %, or between about 0.001±0.0002 wt % and about 1±0.2 wt %, or between about 0.001±0.0002 wt % and about 0.7±0.14 wt %, or between about 0.001±0.0002 wt % and about 0.5±0.1 wt %, or between about 0.001±0.0002 wt % and about 0.3±0.06 wt %, or between about 0.001±0.0002 wt % and about 0.2±0.04 wt %.

The composition according to any preceding or following embodiment, wherein the compound of Formula (III) is a compound of Formula (V):

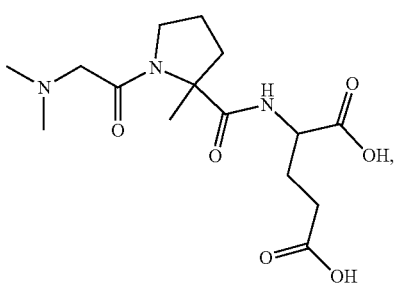

(Me₂-Gly-MePro-Glu)

or a stereoisomer, hydrate, or pharmaceutically acceptable salt thereof.

The composition according to any preceding or following embodiment, wherein the compound of Formula (V), or stereoisomer, hydrate, or pharmaceutically acceptable salt thereof, is present in an amount between about 0.001±0.0002 wt % and about 2±0.4 wt %, or between about 0.001±0.0002 wt % and about 1.5±0.3 wt %, or between about 0.001±0.0002 wt % and about 1±0.2 wt %, or between about 0.001±0.0002 wt % and about 0.7±0.14 wt %, or between about 0.001±0.0002 wt % and about 0.5±0.1 wt %, or between about 0.001±0.0002 wt % and about 0.3±0.06 wt %, or between about 0.001±0.0002 wt % and about 0.2±0.04 wt %.

The composition according to any preceding or following embodiment, wherein the compound of Formula (III) is a compound of Formula (VI):

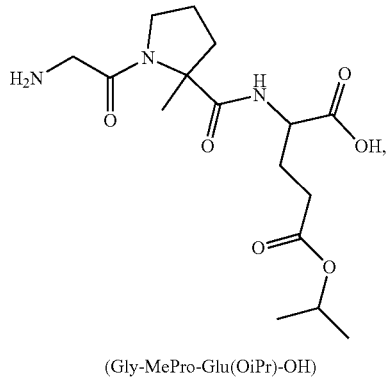

(VI)

(Gly-MePro-Glu(OiPr)-OH)

or a stereoisomer, hydrate, or pharmaceutically acceptable salt thereof.

The composition according to any preceding or following embodiment, wherein the compound of Formula (VI), or stereoisomer, hydrate, or pharmaceutically acceptable salt thereof, is present in an amount between about 0.001±0.0002 wt % and about 2±0.4 wt %, or between about 0.001±0.0002 wt % and about 1.5±0.3 wt %, or between about 0.001±0.0002 wt % and about 1±0.2 wt %, or between about 0.001±0.0002 wt % and about 0.7±0.14 wt %, or between about 0.001±0.0002 wt % and about 0.5±0.1 wt %, or between about 0.001±0.0002 wt % and about 0.3±0.06 wt %, or between about 0.001±0.0002 wt % and about 0.2±0.04 wt %.

The composition according to any preceding or following embodiment, wherein the compound of Formula (III) is a compound of Formula (VII):

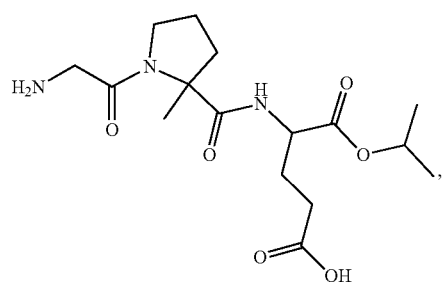

(VII)

(Gly-MePro-Glu-OiPr)

or a stereoisomer, hydrate, or pharmaceutically acceptable salt thereof.

The composition according to any preceding or following embodiment, wherein the compound of Formula (VII) or stereoisomer, hydrate, or pharmaceutically acceptable salt thereof, is present in an amount between about 0.001±0.0002 wt % and about 2±0.4 wt %, or between about 0.001±0.0002 wt % and about 1.5±0.3 wt %, or between about 0.001±0.0002 wt % and about 1±0.2 wt %, or between about 0.001±0.0002 wt % and about 0.7±0.14 wt %, or between about 0.001±0.0002 wt % and about 0.5±0.1 wt %, or between about 0.001±0.0002 wt % and about 0.3±0.06 wt %, or between about 0.001±0.0002 wt % and about 0.2±0.04 wt %.

The composition according to any preceding or following embodiment, wherein the compound of Formula (III) is a compound of Formula (VIII):

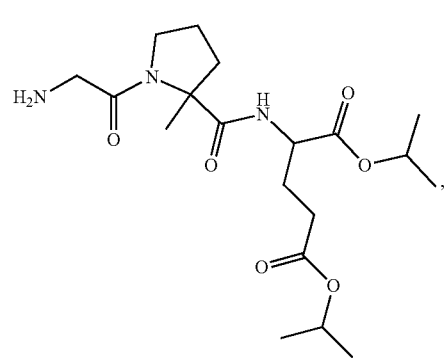

(VIII)

(Gly-MePro-Glu(OiPr)$_2$)

or a stereoisomer, hydrate, or pharmaceutically acceptable salt thereof.

The composition according to any preceding or following embodiment, wherein the compound of Formula (VIII) or stereoisomer, hydrate, or pharmaceutically acceptable salt thereof, is present in an amount between about 0.001±0.0002 wt % and about 2±0.4 wt %, or between about 0.001±0.0002 wt % and about 1.5±0.3 wt %, or between about 0.001±0.0002 wt % and about 1±0.2 wt %, or between about 0.001±0.0002 wt % and about 0.7±0.14 wt %, or between about 0.001±0.0002 wt % and about 0.5±0.1 wt %, or between about 0.001±0.0002 wt % and about 0.3±0.06 wt %, or between about 0.001±0.0002 wt % and about 0.2±0.04 wt %.

A composition comprising a compound of any preceding or following embodiment,

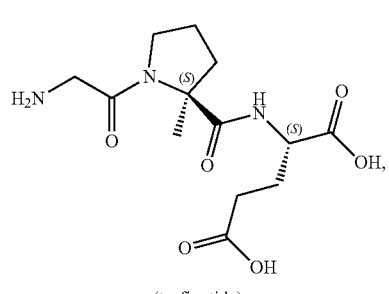

(Ia)

(trofinetide)

said composition obtained by:
a) coupling H-MePro-OH and Z-Gly-OH in the presence of an activating reagent, silylating agent and a solvent, or
b) coupling Z-Gly-OH and Suc-OH and then coupling the obtained Z-Gly-OSu and H-MePro-OH in the absence or presence of an activating reagent, a solvent and in the absence or presence of a silylating agent;
c) coupling the obtained Z-Gly-MePro-OH and H-Glu-OH in the presence of an activating reagent, silylating agent and a solvent;

d) obtaining Z-Gly-MePro-Glu-OH; and e) deprotecting Z-Gly-MePro-Glu-OH, to obtain a composition comprising the compound of Formula (Ia).

The composition according any preceding or following embodiment, wherein the obtained composition is dissolved or suspended in a solvent.

The composition according to either of any preceding or following embodiment, wherein said composition additionally comprises a compound of Formula (II):

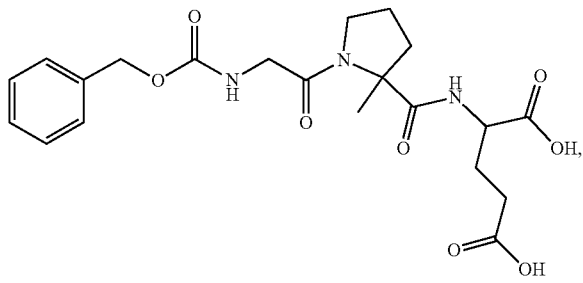

(II)

or a stereoisomer, hydrate, or pharmaceutically acceptable salt thereof; and optionally comprising a compound of Formula (III):

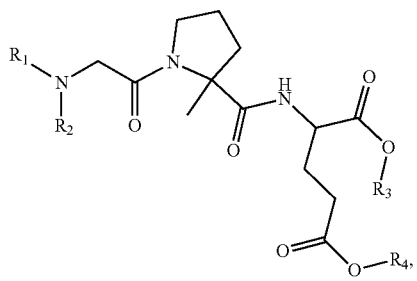

(III)

or a stereoisomer, hydrate, or pharmaceutically acceptable salt thereof, wherein $R_1$, $R_2$, $R_3$ and $R_4$ independently are selected from the group consisting of hydrogen and $C_{1-4}$ alkyl, provided that least one of $R_1$, $R_2$, $R_3$ and $R_4$ is $C_{1-4}$ alkyl.

The composition according to any preceding or following embodiment, wherein the compound of Formula (II), or stereoisomer, hydrate, or pharmaceutically acceptable salt thereof, is absent or present in an amount between about 0.001±0.0002 wt % and about 2±0.4 wt %; and the compound of Formula (III), or stereoisomer, hydrate, or pharmaceutically acceptable salt thereof, is absent or present in an amount between about 0.001±0.0002 wt % and about 2±0.4 wt %, provided that at least one of the compounds of Formula (II) or (III), or stereoisomer, hydrate, or pharmaceutically acceptable salt thereof, is present.

The composition according to any preceding or following embodiment, wherein the compound of Formula (II), or stereoisomer, hydrate, or pharmaceutically acceptable salt thereof, is present in an amount of between about 0.001±0.0002 wt % and about 0.3±0.06 wt %.

The composition according to any preceding or following embodiment, wherein the compound of Formula (II), or stereoisomer, hydrate, or pharmaceutically acceptable salt thereof, is present in an amount between about 0.001±0.0002 wt % and about 0.1±0.02 wt %.

The composition according to any preceding or following embodiment, wherein the compound of Formula (II), or stereoisomer, hydrate, or pharmaceutically acceptable salt thereof, is present in an amount between about 0.001±0.0002 wt % and about 2±0.4 wt %, or between about 0.001±0.0002 wt % and about 1.5±0.3 wt %, or between about 0.001±0.0002 wt % and about 1±0.2 wt %, or between about 0.001±0.0002 wt % and about 0.7±0.14 wt %, or between about 0.001±0.0002 wt % and about 0.5±0.1 wt %, or between about 0.001±0.0002 wt % and about 0.3±0.06 wt %, or between about 0.001±0.0002 wt % and about 0.2±0.04 wt %.

The composition according to any preceding or following embodiment, wherein the compound according to Formula (II) is a compound of Formula (IIa):

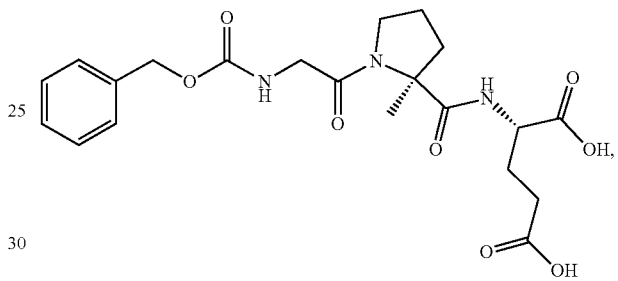

(IIa)

(Z-Gly-MePro-Glu-OH)

or a hydrate, or pharmaceutically acceptable salt thereof.

The composition according to any preceding or following embodiment wherein the compound of Formula (II), or stereoisomer, hydrate, or pharmaceutically acceptable salt thereof, is absent.

The composition according to any preceding or following embodiment, wherein the compound of Formula (III), or stereoisomer, hydrate, or pharmaceutically acceptable salt thereof, is present in an amount between about 0.001±0.0002 wt % and about 2.0±0.4 wt %.

The composition according to any preceding or following embodiment, where said silylating agent does not contain a cyano group.

The composition according to any preceding or following embodiment, where said silylating agent is selected from the group consisting of N,O-bis(trimethylsilyl)acetamide, N,O-bis(trimethylsilyl)trifluoroacetamide, hexamethyldisilazane, N-methyl-N-(trimethylsilyl)acetamide, N.-methyl-N-(trimethylsilyl)trifluoroacetamide, N-(trimethylsilyl)acetamide, N-(trimethylsilyl)diethylamine, N-(trimethylsilyl)dimethylamine, 1-(trimethylsilyl)imidazole, and 3-(trimethylsilyl)2-oxazolidone.

The composition according to any preceding or following embodiment wherein said solvent in step a) is a polar organic solvent, or a polar aprotic organic solvent.

The composition according to any preceding or following embodiment wherein said solvent in step b) is a polar organic solvent, or a polar aprotic organic solvent.

The composition according to any preceding or following embodiment wherein said solvent in step c) is a polar organic solvent, or a polar aprotic organic solvent.

The composition according to any preceding or following embodiment wherein the solvent is selected from the group consisting of alkyl acetates, chlorinated hydrocarbons, alkyl cyanides and amide type solvents, or mixture thereof.

The composition according to any preceding or following embodiment wherein said activating reagent is selected from the group consisting of carbodiimides, acyl halides, phosphonium salts, uronium salts and guanidinium salts.

The composition according to any preceding or following embodiment, wherein deprotecting is achieved by hydrogenation.

The composition according to any preceding or following embodiment, wherein hydrogenation is performed in the presence of a Pd/C catalyst.

The composition according to any preceding or following embodiment, wherein hydrogenation is performed in the presence of a Pd/Si catalyst.

The composition according to any preceding or following embodiment, wherein hydrogenation is performed at a temperature from about 10-40° C., or a temperature of about 20-30° C., or a temperature of about 25° C.

The composition according to any preceding or following embodiment, wherein hydrogenation is performed at about 0 to about 6 bars of pressure.

The composition according to any preceding or following embodiment, wherein the hydrogenation is performed using at least one solvent selected from the group consisting of water, ethyl acetate, isopropyl acetate, methanol, ethanol, isopropanol, or mixtures thereof.

The composition according to any preceding or following embodiment, comprising at least 90 wt %, such as at least 91 wt %, 92 wt %, 93 wt %, 94 wt %, 95 wt %, 96 wt %, and 97 wt %, of the compound of Formula (I) or a stereoisomer, hydrate, or pharmaceutically acceptable salt thereof, on an anhydrous basis.

The composition according to any preceding or following embodiment, comprising at least 90 wt %, such as at least 91 wt %, 92 wt %, 93 wt %, 94 wt %, 95 wt %, 96 wt %, and 97 wt %, of the compound of Formula (Ia) or a hydrate, or pharmaceutically acceptable salt thereof, on an anhydrous basis.

A composition comprising at least 90 wt %, such as at least 91 wt %, 92 wt %, 93 wt %, 94 wt %, 95 wt %, 96 wt %, and 97 wt %, of the compound of Formula (I) or a stereoisomer, hydrate, or pharmaceutically acceptable salt thereof, on an anhydrous basis.

A composition comprising at least 90 wt %, such as at least 91 wt %, 92 wt %, 93 wt %, 94 wt %, 95 wt %, 96 wt %, and 97 wt %, of the compound of Formula (Ia) or a hydrate, or pharmaceutically acceptable salt thereof, on an anhydrous basis.

A composition according to any preceding or following embodiment, comprising a compound of Formula (I)

or a stereoisomer, hydrate, or pharmaceutically acceptable salt thereof, and a compound of Formula (II):

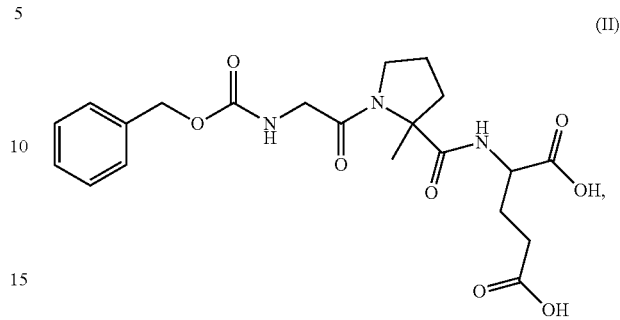

(II)

or a stereoisomer, hydrate, or pharmaceutically acceptable salt thereof, and/or a compound of Formula (III):

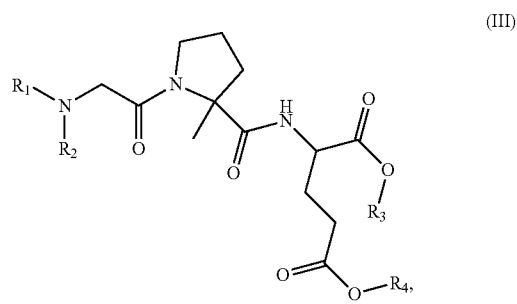

(III)

or a stereoisomer, hydrate, or pharmaceutically acceptable salt thereof, wherein $R_1$, $R_2$, $R_3$ and $R_4$ independently are selected from the group consisting of hydrogen and $C_{1-4}$ alkyl, provided that least one of $R_1$, $R_2$, $R_3$ and $R_4$ is $C_{1-4}$ alkyl, and wherein the composition comprises at least 90 wt %, such as 91 wt %, 92 wt %, 93 wt %, 94 wt %, 95 wt %, 96 wt %, or 97 wt % of the compound of Formula (I) on an anhydrous basis.

A composition according to any preceding or following embodiment, comprising a compound of Formula (Ia)

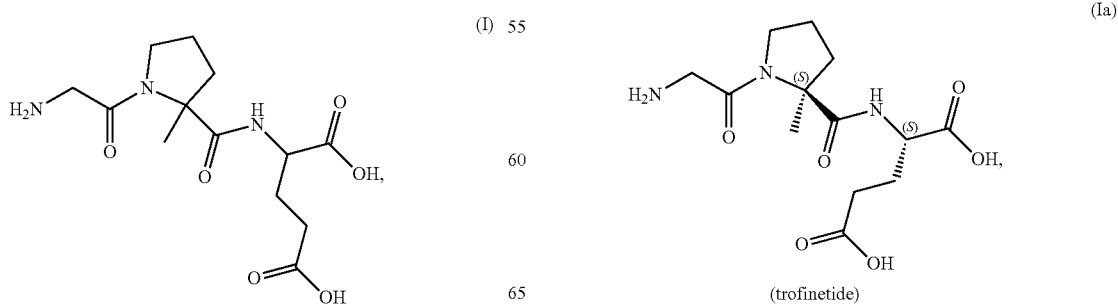

(trofinetide)

or a hydrate, or pharmaceutically acceptable salt thereof, and a compound of Formula (II):

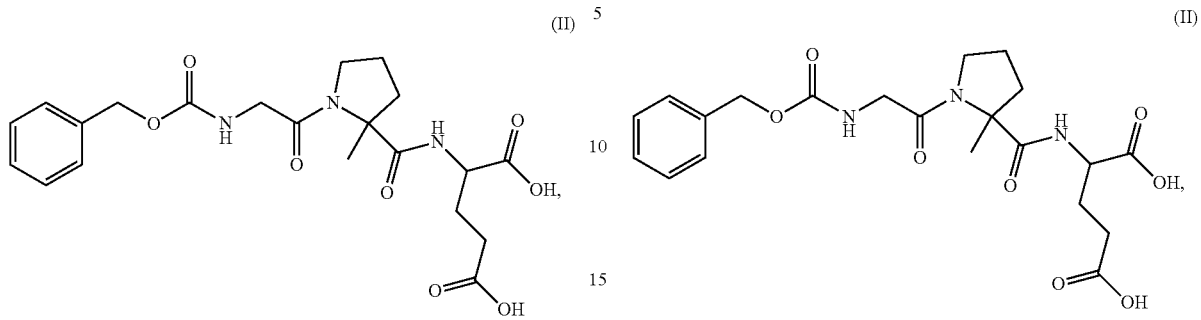
(II)

or a stereoisomer, hydrate, or pharmaceutically acceptable salt thereof, and/or a compound of Formula (III):

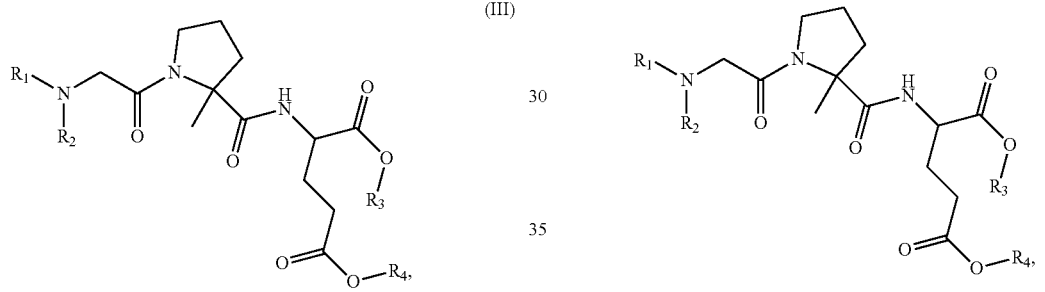
(III)

or a stereoisomer, hydrate, or pharmaceutically acceptable salt thereof, wherein $R_1$, $R_2$, $R_3$ and $R_4$ independently are selected from the group consisting of hydrogen and $C_{1-4}$ alkyl, provided that least one of $R_1$, $R_2$, $R_3$ and $R_4$ is $C_{1-4}$ alkyl, and wherein the composition comprises at least 90 wt %, such as 91 wt %, 92 wt %, 93 wt %, 94 wt %, 95 wt %, 96 wt %, or 97 wt % of the compound of Formula (Ia) on an anhydrous basis.

A composition comprising a compound of Formula (I)

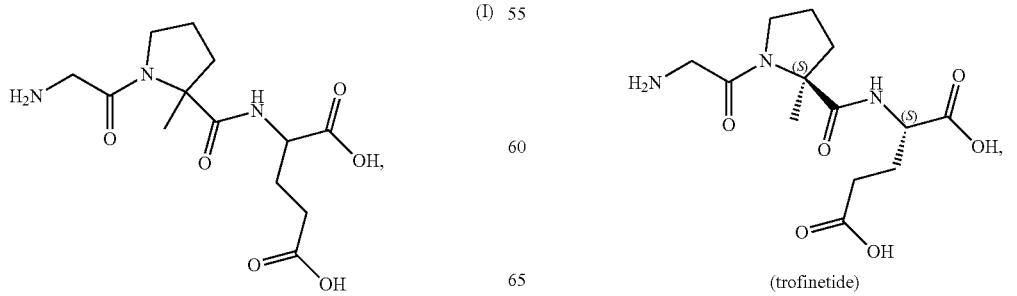
(I)

or a stereoisomer, hydrate, or pharmaceutically acceptable salt thereof, and a compound of Formula (II):

(II)

or a stereoisomer, a hydrate, or pharmaceutically acceptable salt thereof, and/or a compound of Formula (III):

(III)

or a stereoisomer, hydrate, or pharmaceutically acceptable salt thereof, wherein $R_1$, $R_2$, $R_3$ and $R_4$ independently are selected from the group consisting of hydrogen and $C_{1-4}$ alkyl, provided that least one of $R_1$, $R_2$, $R_3$ and $R_4$ is $C_{1-4}$ alkyl, and wherein the compositions comprises at least 90 wt %, such as 91 wt %, 92 wt %, 93 wt %, 94 wt %, 95 wt %, 96 wt %, or 97 wt % of the compound of Formula (I) on an anhydrous basis.

A composition comprising a compound of Formula (Ia)

(Ia)

(trofinetide)

or a hydrate, or pharmaceutically acceptable salt thereof, and a compound of Formula (II):

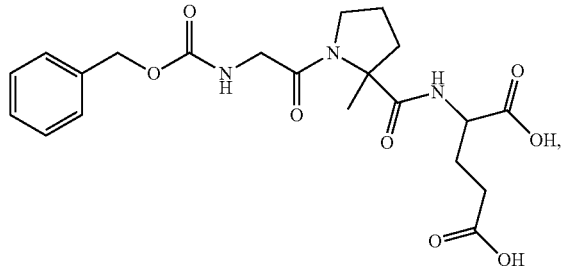

or a stereoisomer, hydrate, or pharmaceutically acceptable salt thereof, and/or a compound of Formula (III):

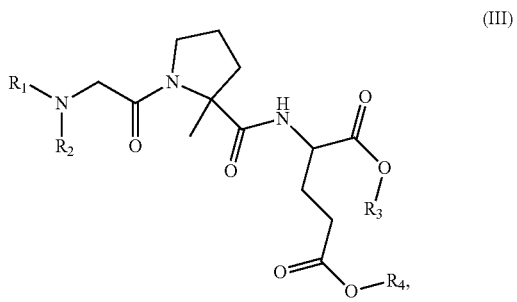

or a stereoisomer, hydrate, or pharmaceutically acceptable salt thereof, wherein $R_1$, $R_2$, $R_3$ and $R_4$ independently are selected from the group consisting of hydrogen and $C_{1-4}$ alkyl, provided that least one of $R_1$, $R_2$, $R_3$ and $R_4$ is $C_{1-4}$ alkyl, and wherein the composition comprises at least 90 wt % such as 91 wt %, 92 wt %, 93 wt %, 94 wt %, 95 wt %, 96 wt %, or 97 wt % of the compound of Formula (Ia) on an anhydrous basis.

A method of manufacturing a composition containing trofinetide according to any preceding or following embodiment comprising the steps:

a) coupling H-MePro-OH and Z-Gly-OH in the presence of an activating agent, silylating agent and a solvent; or b) coupling Z-Gly-OH and Suc-OH and then coupling the obtained Z-Gly-OSu and H-MePro-OH in the absence or presence of an activating reagent, a solvent and in the absence or presence of a silylating agent;

c) coupling the obtained Z-Gly-MePro-OH and H-Glu-OH in the presence of an activating reagent, silylating agent and a solvent;

d) obtaining Z-Gly-MePro-Glu-OH; and e) deprotecting Z-Gly-MePro-Glu-OH, thereby producing trofinetide, wherein trofinetide is dissolved or suspended in a solvent.

The method of any preceding or following embodiment, where said silylating agent does not contain a cyano group.

The method of any preceding or following embodiment, wherein said silylating agent is selected from the group consisting of N,O-bis(trimethylsilyl)acetamide, N,O-bis(trimethylsilyl)trifluoroacetamide, hexamethyldisilazane, N-methyl-N-(trimethylsilyl)acetamide (TMA), N.-methyl-N-(trimethylsilyl)trifluoroacetamide, N-(trimethylsilyl)acetamide, N-(trimethylsilyl)diethylamine, N-(trimethylsilyl)di-methylamine, 1-(trimethylsilyl)imidazole, and 3-(trimethylsilyl)2-oxazolidone.

The method of any preceding or following embodiment wherein said solvent in step a) is a polar organic solvent, or a polar aprotic organic solvent.

The method of any preceding or following embodiment wherein said solvent in step b) is a polar organic solvent, or a polar aprotic organic solvent.

The method of any preceding or following embodiment wherein said solvent in step c) is a polar organic solvent, or a polar aprotic organic solvent.

The method of any preceding or following embodiment wherein the solvent is selected from the group consisting of alkyl acetates, chlorinated hydrocarbons, alkyl cyanides and amide type solvents, or mixture thereof.

The method of any preceding or following embodiment wherein said activating reagent is selected from the group consisting of carbodiimides, acyl halides, phosphonium salts, uronium salts and guanidinium salts.

The method of any preceding or following embodiment, wherein deprotecting is achieved by hydrogenation.

The method of any preceding or following embodiment, wherein hydrogenation is performed in the presence of a Pd/C catalyst.

The method of any preceding or following embodiment, wherein hydrogenation is performed in the presence of a Pd/Si catalyst.

The method of any preceding or following embodiment, wherein hydrogenation is performed at a temperature from about 10-40° C., or a temperature of about 20-30° C., or a temperature of about 25° C.

The method of any preceding or following embodiment, wherein hydrogenation is performed at about 0 to about 6 bars of pressure.

The method of any preceding or following embodiment, wherein the hydrogenation is performed in at least one solvent selected from the group consisting of water, ethyl acetate, isopropyl acetate, methanol, ethanol, isopropanol, or mixtures thereof.

A product comprising a composition according to any preceding or following embodiment.

A product according to any preceding or following embodiment wherein the product is a kit.

A kit containing a dosage form of any preceding or following embodiment comprising a compound of Formula (Ia),

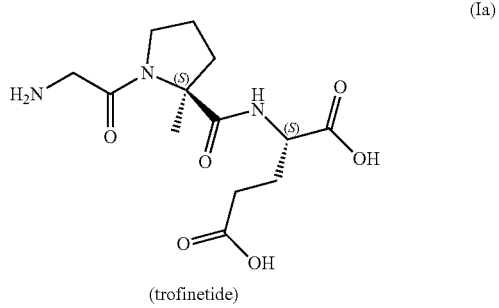

(trofinetide)

and a compound of Formula (IIa), or a hydrate, or pharmaceutically acceptable salt thereof:

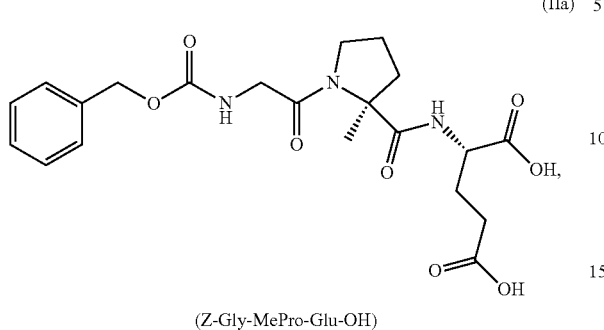

(Z-Gly-MePro-Glu-OH)

or a hydrate, or pharmaceutically acceptable salt thereof, and instructions for administration to a subject in need thereof.

The kit of any preceding or following embodiment, further comprising one or more compounds selected from the group consisting of Formula (III), Formula (IIIa), Formula (IV), Formula (V), Formula (VI), Formula (VII), Formula (VIII), and Formula (IX).

A product of any preceding or following embodiment, including a kit containing a dosage form with instructions for use, comprising a compound of Formula (Ia)

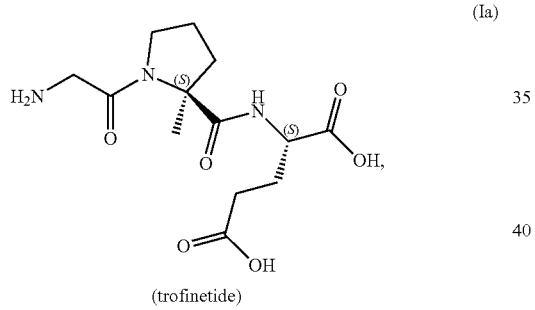

(trofinetide)

or a hydrate, or pharmaceutically acceptable salt thereof, and a compound of Formula (IIa)

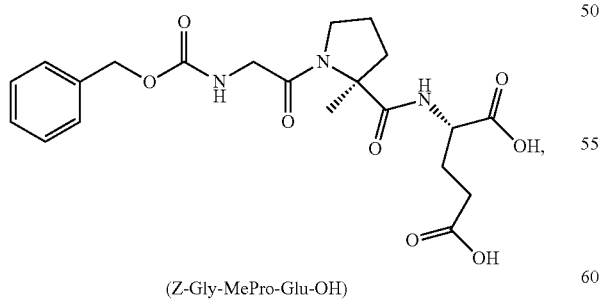

(Z-Gly-MePro-Glu-OH)

or a hydrate, or pharmaceutically acceptable salt thereof, wherein the product comprises between 95 wt % and 105 wt %, such as 96 wt %, 97 wt %, 98 wt %, 99 wt %, 100 wt %, 101 wt %, 102 wt %, 103 wt %, or 104 wt % of the specified amount of the compound of Formula (Ia) in the product.

A product of any preceding embodiment, including a kit containing a dosage form with instructions for use, comprising a compound of Formula (Ia)

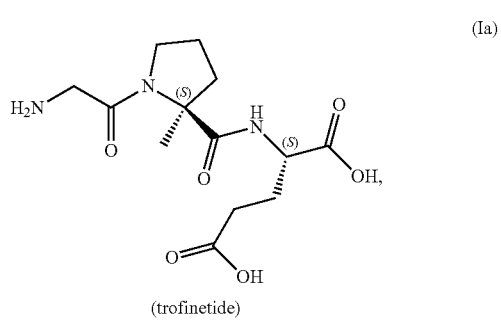

(trofinetide)

or a hydrate, or pharmaceutically acceptable salt thereof, and a compound of Formula (IIa)

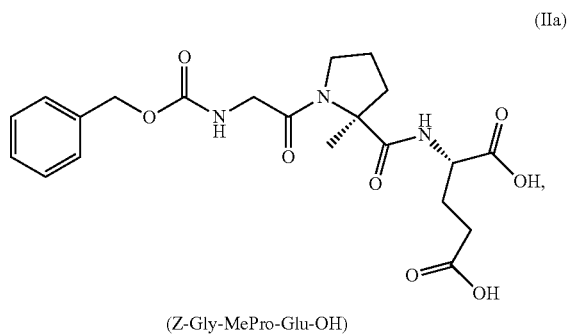 [SMILES: C[C@@]1(C(=O)N[C@@H](CCC(=O)O)C(=O)O)CCCN1C(=O)CNC(=O)OCc1ccccc1]

(Z-Gly-MePro-Glu-OH)

or a hydrate, or pharmaceutically acceptable salt thereof, and additionally comprising one or more compounds selected from the group consisting of Formula (III), Formula (IIIa), Formula (IV), Formula (V), Formula (VI), Formula (VII), Formula (VIII), and Formula (IX), wherein the composition comprises between 95 wt % and 105 wt %, such as 96 wt %, 97 wt %, 98 wt %, 99 wt %, 100 wt %, 101 wt %, 102 wt %, 103 wt %, or 104 wt % of the specified amount of the compound of Formula (Ia) in the product.

A product, including a kit containing a dosage form with instructions for use, comprising a compound of Formula (Ia)

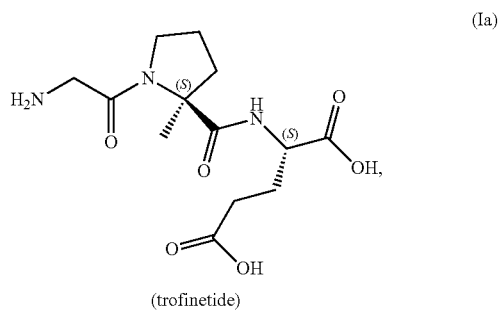

(trofinetide)

or a hydrate, or pharmaceutically acceptable salt thereof, and a compound of Formula (IIa)

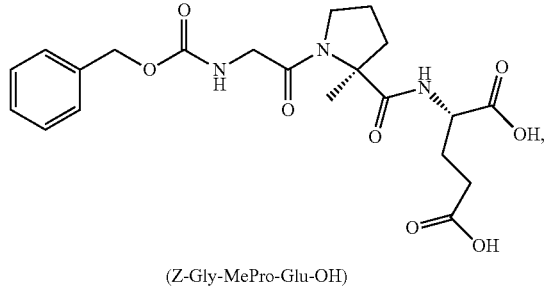

(Z-Gly-MePro-Glu-OH)

(IIa)

or a hydrate, or pharmaceutically acceptable salt thereof, wherein the product comprises between 95 wt % and 105 wt %, such as 96 wt %, 97 wt %, 98 wt %, 99 wt %, 100 wt %, 101 wt %, 102 wt %, 103 wt %, or 104 wt % of the specified amount of the compound of Formula (Ia) in the product.

A product, including a kit containing a dosage form with instructions for use, comprising a compound of Formula (Ia)

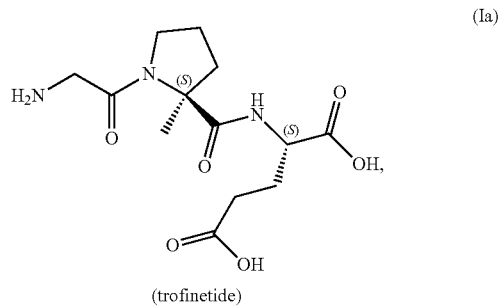

(trofinetide)

(Ia)

or a hydrate, or pharmaceutically acceptable salt thereof, and a compound of Formula (IIa)

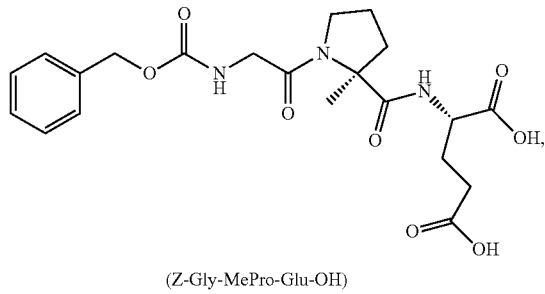

(Z-Gly-MePro-Glu-OH)

(IIa)

or a hydrate, or pharmaceutically acceptable salt thereof, and additionally comprising one or more compounds selected from the group consisting of Formula (III), Formula (IIIa), Formula (IV), Formula (V), Formula (VI), Formula (VII), Formula (VIII), and Formula (IX), wherein the composition comprises between 95 wt % and 105 wt %, such as 96 wt %, 97 wt %, 98 wt %, 99 wt %, 100 wt %, 101 wt %, 102 wt %, 103 wt %, or 104 wt % of the specified amount of the compound of Formula (Ia) in the product.

Manufacture of Compounds and Compositions of Formula (I)

Manufacture of compounds of this disclosure will produce compounds having stereochemistry defined by the stereochemistry of the reactants, and as such will be well understood by those skilled in the art. In situations where the reactants have mixed stereochemistry, e.g. racemates, or other permutations of stereoisomers thereof, compounds obtained will have correspondingly mixed stereochemistry. In certain embodiments and aspects relating to compounds and compositions disclosed herein the stereochemistry have been indicated, in others not. Whenever a formula or chemical structure is silent about the stereochemistry of the compounds and/or compositions it should be understood as relating to all possible stereochemical aspects.

It is to be understood that the processes described herein are only specific steps. Other schemes can be developed to manufacture compounds of Formula I.

Manufacture of Trofinetide (Formula (Ia))

A method of manufacturing a composition containing trofinetide generally includes the steps:
a) coupling H-MePro-OH and Z-Gly-OH in the presence of an activating reagent, silylating agent and a solvent, or
b) coupling Z-Gly-OH and Suc-OH and then coupling the obtained Z-Gly-OSu and H-MePro-OH in the absence or presence of an activating reagent, a solvent and in the absence or presence of a silylating agent;
c) coupling the obtained Z-Gly-MePro-OH and H-Glu-OH in the presence of an activating reagent, silylating agent and a solvent;
d) obtaining Z-Gly-MePro-Glu-OH at a conversion of at least 95%; and
e) deprotecting Z-Gly-MePro-Glu-OH, wherein Z-Gly-MePro-Glu-OH is dissolved or suspended in a solvent to produce trofinetide.

These general steps are described in more detail in the Examples below.

Production of Other Compounds

Along with the compound of Formula (I), certain other products can be produced and be present in a composition disclosed herein. An example of a compound or stereoisomer of Formula (I) is of Formula (Ia) (trofinetide). Other products include Compounds (II), (IIa), (III), (IIIa), (IV), (V), (VI), (VII), (VIII) and (IX) as described above.

Additional products include kits containing a dosage form comprising a compound of Formula (Ia) (trofinetide) and a compound of Formula (IIa) and instructions for use.

A kit may additionally comprise one or more compounds selected from the group consisting of Formula (III), Formula (IIIa), Formula (IV), Formula (V), Formula (VI), Formula (VII), Formula (VIII), and Formula (IX).

EXAMPLES

Manufacture of compositions including trofinetide are exemplified by the following. It can be understood that other schemes can be used to produce trofinetide.

Example 1: Trofinetide Manufacturing Process

In general, trofinetide and related compounds can be manufactured from a precursor peptide or amino acid reacted with a silylating or persilylating agent at one or more steps. In the present invention, one can use silylating agents, such as N-trialkylsilyl amines or N-trialkylsilyl amides, not containing a cyano group.

Examples of such silylating reagents include N,O-bis (trimethylsilyl)acetamide (BSA), N,O-bis(trimethylsilyl)trifluoroacetamide, hexamethyldisilazane, N-methyl-N-(trimethylsilyl)acetamide (TMA), N-methyl-N-(trimethylsilyl)trifluoroacetamide, N-(trimethylsilyl)acetamide, N-(trimethylsilyl)diethylamine, N-(trimethylsilyl)dimethylamine, 1-(trimethylsilyl)imidazole, 3-(trimethylsilyl)-2-oxazolidone.

Step 1: Preparation of Z-Gly-OSu
Several alternative procedures can be used for this step.
Procedure 1A

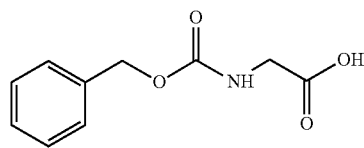

Z-Gly-OH
Molecular Formula: C$_{10}$H$_{11}$NO$_4$
Formula Weight: 209.19864

1. SucOH
2. EDC·HCl
   iPrOH

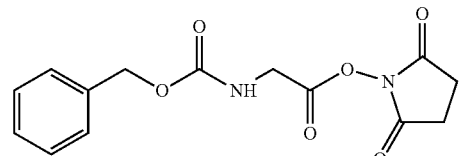

Z-Gly-OSu
Molecular Formula: C$_{14}$H$_{14}$N$_2$O$_6$
Formula Weight: 306.27076

One (1) eq of Z-Gly-OH and 1.1 eq of Suc-OH were solubilized in 27 eq of iPrOH and 4 eq of CH$_2$Cl$_2$ at 21° C. The mixture was cooled and when the temperature reached −4° C., 1.1 eq of EDC·HCl was added gradually, keeping the temperature below 10° C. During the reaction a dense solid appeared. After addition of EDC·HCl, the mixture was allowed to warm to 20° C. The suspension was cooled to 11° C. and filtered. The cake was washed with 4.9 eq of cold iPrOH and 11 eq of IPE before drying at 34° C. (Z-Gly-OSu dried product—Purity: 99.5%; NMR assay: 96%; Yield: 84%).

Procedure 1B
This Procedure is for a variant of Procedure 1A, and differs by replacing iPrOH with ACN. One (1) eq of Z-Gly-OH and 1.1 eq of Suc-OH were solubilized in 22 eq of ACN at 35° C. The mixture was cooled in an ice bath. When the temperature reached 1° C., 0.9 eq of DCC in 5.5 eq of ACN was added gradually to keep the temperature below 5° C. The coupling reaction took about 20 hrs. During the reaction, DCU precipitated and was removed by filtration at the end of the coupling. After filtration, DCU was washed with ACN to recover the product. The mixture of Z-Gly-OSu was then concentrated to reach 60% by weight. iPrOH (17 eq) was added to initiate the crystallization. Quickly after iPrOH addition a dense solid appeared. An additional 17 eq of iPrOH was needed to liquify the suspension. The suspension was cooled in an ice bath and filtered. The solid was washed with 9 eq of iPrOH before drying at 45° C. (Z-Gly-OSu dried product—Purity: 99.2%; HPLC assay: 99.6%; Yield: 71%).

Step 2: Preparation of Z-Gly-MePro-OH
Several alternative procedures can be used for this step.
Procedure 2A

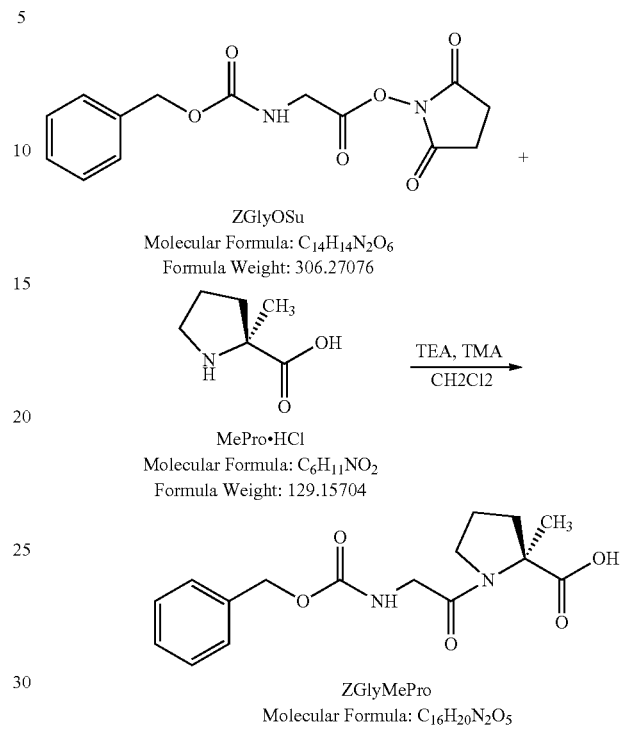

One (1) eq of MePro·HCl was partially solubilized in 29 eq of CH$_2$Cl$_2$ at 35° C. with 1.04 eq of TEA and 1.6 eq of TMA. The mixture was heated at 35° C. for 2 hrs to perform the silylation. Then 1.02 eq of Z-Gly-OSu was added to the mixture. The mixture was kept at 35° C. for 3 hrs and then 0.075 eq of butylamine was added to quench the reaction. The mixture was allowed to return to room temperature and mixed for at least 15 min. The Z-Gly-MePro-OH was extracted once with 5% w/w NaHCO$_3$ in 186 eq of water, then three times successively with 5% w/w NaHCO$_3$ in 62 eq of water. The aqueous layers were pooled and the pH was brought to 2.2 by addition of 34 eq of HCl as 12N HCl at room temperature. At this pH, Z-Gly-MePro-OH formed a sticky solid that was solubilized at 45° C. with approximately 33 eq of EtOAc and 2.3 eq of iButOH. Z-Gly-MePro-OH was extracted into the organic layer and washed with 62 eq of demineralized water. The organic layer was then dried by azeotropic distillation with 11.5 eq of EtOAc until the peptide began to precipitate.

Cyclohexane (12 eq) was added to the mixture to complete the precipitation. The suspension was cooled at 5° C. for 2 hrs and filtered. The solid was washed with 10 eq of cyclohexane before drying at 45° C. (Z-Gly-MePro-OH dried product—Purity: 100%; HPLC assay: 100%; Yield 79%).

Procedure 2B
This Procedure is for a variant of Procedure 2A. One (1) eq of MePro·HCl was partially solubilized in 36.6 eq of CH$_2$Cl$_2$ at 34° C. with 1.01 eq of TEA and 0.1 eq of TMA. Then 1.05 eq of Z-Gly-OSu was added to the mixture, followed by 1.0 eq of TEA. The mixture was maintained at 35° C. for approximately 1 hr, cooled to 25 to 30° C. and 0.075 eq of DMAPA was added to stop the reaction. One hundred (100) eq of water, 8.6 eq of HCl as 12N HCl and 0.3 eq of KHSO$_4$ were added to the mixture (no precipitation was observed, pH=1.7). Z-Gly-MePro-OH was extracted into the organic layer and washed twice with 97 eq of demineralized water with 0.3 eq of KHSO$_4$, then 100 eq of demineralized water, respectively. EtOAc (23 eq) was added to the mixture and CH$_2$Cl$_2$ was removed by distillation until the peptide began to precipitate. Cyclohexane (25 eq) was added to the mixture to complete the precipitation. The suspension was cooled at −2° C. overnight and filtered. The solid was washed with 21 eq of cyclohexane before drying at 39° C. (Z-Gly-MePro-OH dried product—Purity: 98.7%; NMR assay: 98%; Yield 86%).

Procedure 2C

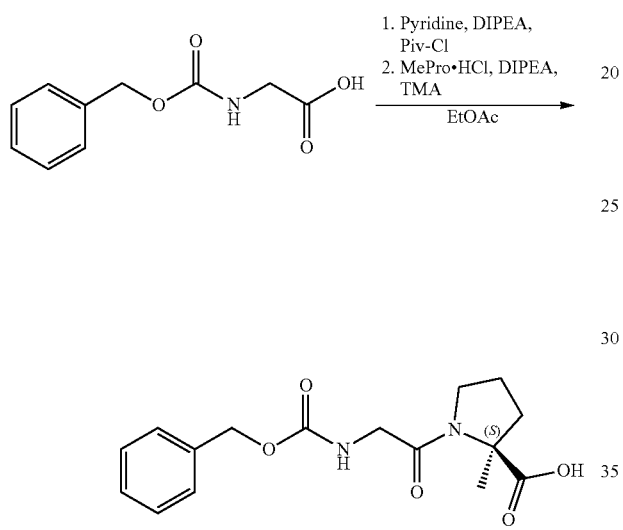

In reactor 1, MePro·HCl (1 eq) was suspended in EtOAc (about 7 eq). DIPEA (1 eq) and TMA (2 eq) were added, and the mixture heated to dissolve solids. After dissolution, the solution was cooled to 0° C. In reactor 2, Z-Gly-OH (1 eq) was suspended in EtOAc (about 15 eq). DIPEA (1 eq), and pyridine (1 eq) were added. After mixing, a solution was obtained, and cooled to −5° C. Piv-Cl (1 eq) was added to reactor 2, and the contents of reactor 1 added to reactor 2. Upon completed addition, the contents of reactor 2 were taken to room temperature. The conversion from Z-Gly-OH to Z-Gly-MePro-OH was monitored by HPLC. When the reaction was complete, the reaction mixture was quenched with DMAPA (0.1 eq), and washed with an aqueous solution comprised of KHSO$_4$, (about 2.5 wt %), NaCl (about 4 wt %), and conc. HCl (about 6 wt %) in 100 eq H$_2$O. The aqueous layer was re-extracted with EtOAc, and the combined organic layers washed with an aqueous solution comprised of KHSO$_4$ (about 2.5 wt %) and NaCl (about 2.5 wt %) in 100 eq H$_2$O, and then with water (100 eq). Residual water was removed from the organic solution of Z-Gly-MePro-OH by vacuum distillation with EtOAc. The resulting suspension was diluted with heptane (about 15 eq) and cooled to 0° C. The product was isolated by filtration, washed with cold heptane (about 7 eq), and dried under vacuum at 45° C. Z-Gly-MePro-OH (85% yield) was obtained.

Step 3: Preparation of Z-Gly-MePro-Glu-OH
Several alternative procedures can be used in this step.
Procedure 3A

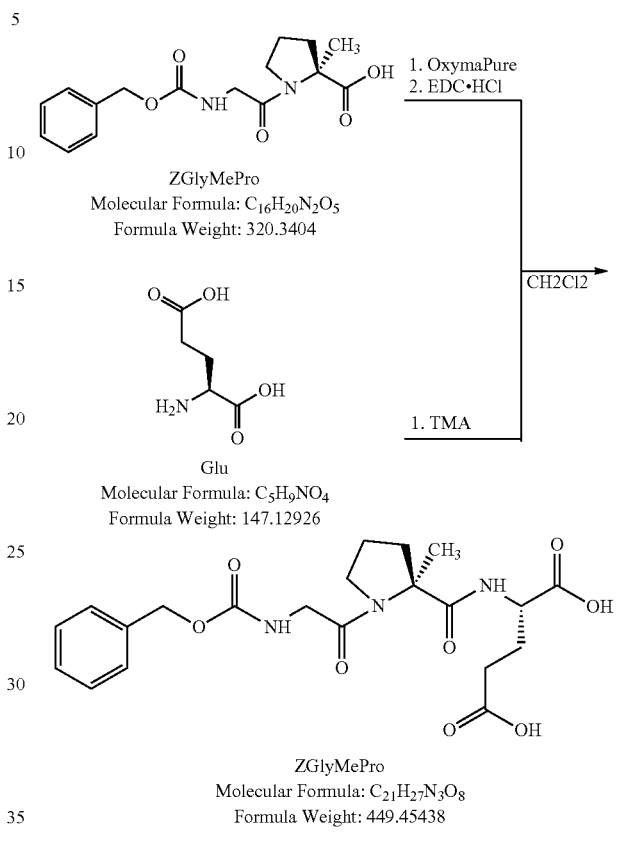

H-Glu-OH (1.05 eq) was silylated in 2 eq of CH$_2$Cl$_2$ with 3.5 eq of TMA at 65° C. Silylation was completed after 2 hrs. While the silylation was ongoing, 1.0 eq of Z-Gly-MePro-OH and 1.0 eq of Oxyma Pure were solubilized in 24 eq of CH$_2$Cl$_2$ and 1.0 eq of DMA at room temperature in another reactor. EDC·HCl (1.0 eq.) was added. The activation rate reached 97% after 15 min. The activated Oxyma Pure solution, was then added to silylated H-Glu-OH at 40° C. and cooled at room temperature. Coupling duration was approximately 15 min, with a coupling rate of 97%. Addition of 8.2% w/w NaHCO$_3$ in 156 eq of water to the mixture at room temperature (with the emission of CO$_2$) was performed to reach pH 8. Z-Gly-MePro-Glu-OH was extracted in water. The aqueous layer was washed twice with 29 eq of CH$_2$Cl$_2$. Residual CH$_2$Cl$_2$ was removed by concentration. The pH was brought to 2.5 with 2.5N HCl, followed by 1.4 eq of solid KHSO$_4$ to precipitate Z-Gly-MePro-Glu-OH. The mixture was filtered and the solid was washed with 3×52 eq of water.

The filtered solid was added to 311 eq of demineralized water and heated to 55-60° C. iPrOH (29 eq) was added gradually until total solubilization of the product. The mixture was slowly cooled to 10° C. under moderate mixing during 40 min to initiate the crystallization. The peptide was filtered and washed with 2×52 eq of water before drying at 45° C. (Z-Gly-MePro-Glu-OH dried product—Purity: 99.5%; NMR assay: 96%; Yield 74%).

Procedure 3B
One (1) eq of Z-Gly-MePro-OH and 1.05 eq of Suc-OH were solubilized in 40 eq of ACN and 30 eq of CH$_2$Cl$_2$ at room temperature. The mixture was cooled in an ice bath, and when the temperature was near 0° C., 1.05 eq of DCC dissolved in 8 eq of ACN was added gradually, keeping the temperature below 5° C. After addition of DCC, the mixture was progressively heated from 0° C. to 5° C. over 1 hr, then to 20° C. between 1 to 2 hrs and then to 45° C. between 2 to 5 hrs. After 5 hrs, the mixture was cooled to 5° C. and maintained overnight. The activation rate reached 98% after approximately 24 hrs. DCU was removed by filtration and washed with 13.5 eq of ACN. During the activation step, 1.1 eq of H-Glu-OH was silylated in 30 eq of ACN with 2.64 eq of TMA at 65° C. Silylation was completed after 2 hrs. Z-Gly-MePro-OSu was then added gradually to the silylated H-Glu-OH at room temperature, with 0.4 eq of TMA added to maintain the solubility of the H-Glu-OH. The mixture was heated to 45° C. and 0.7 eq of TMA was added if precipitation occurred. The coupling duration was about 24 hrs to achieve a coupling rate of approximately 91%. The reaction was quenched by addition of 0.15 eq of butylamine and 2.0 eq of TEA. Water (233 eq) was added and the mixture concentrated until gelation occurred. Z-Gly-MePro-Glu-OH was extracted in water by addition of 5% w/w NaHCO₃ in 233 eq of water and 132 eq of CH₂Cl₂. The aqueous layer was washed twice with 44 eq of CH₂Cl₂. Residual CH₂Cl₂ was removed by distillation. The pH was brought to 2.0 with 24 eq of HCl as 12N HCl followed by 75 eq of HCl as 4N HCl. At this pH, Z-Gly-MePro-Glu-OH precipitated. The mixture was cooled in an ice bath over 1 hr and filtered. The solid was washed with 186 eq of cold water before drying at 45° C. (Z-Gly-MePro-Glu-OH dried product—HPLC Purity: 98.4%; NMR assay: 100%; Yield 55%).

Procedure 3C

This Procedure is for a variant of Procedure 3A. H-Glu-OH (1.05 eq) was silylated in 3.7 eq of CH₂Cl₂ with 3.5 eq of TMA at 62° C. Silylation was completed after approximately 1.5 to 2 hrs, as evidenced by solubilization. During the silylation step, 1.0 eq of Z-Gly-MePro-OH and 1.0 eq of Oxyma Pure were solubilized in 31.5 eq of CH₂Cl₂ at 22° C. One (1.06) eq of EDC·HCl was added to complete the activation. The silylated H-Glu-OH was then added to the activated Oxyma Pure solution. The temperature was controlled during the addition to stay below 45° C. Desilylation was performed by addition of a mixture of 2.5% w/w KHSO₄ in 153 eq of water and 9 eq of iPrOH to reach a pH of 1.65. Residual CH₂Cl₂ was removed by concentration. The mixture was cooled to 12° C. to precipitate the Z-Gly-MePro-Glu-OH. The mixture was filtered and the solid was washed with 90 eq of water before drying at 36° C.

Procedure 3D

This Procedure is for a variant of Procedure 3A. H-Glu-OH (1.05 eq.) was silylated in 3.9 eq of CH₂Cl₂ with 3.5 eq of TMA at 62° C. Silylation was completed after 2 hrs, as evidenced by Solubilization. During the silylation step, 1 eq of Z-Gly-MePro-OH and 1 eq of Oxyma Pure were solubilized in 25 eq of CH₂Cl₂ at 23° C. One (1) eq of EDC·HCl was added. To complete the activation, an additional 0.07 eq of EDC. HCl was added. Silylated H-Glu-OH was then added to the activated Oxyma Pure solution. Temperature was controlled during the addition to stay below 45° C. Desilylation was performed by addition of a mixture of 2.5% w/w KHSO₄ in 160 eq of water and 9.6 eq of iPrOH to reach pH 1.63.

Residual CH₂Cl₂ was removed by concentration. The mixture was cooled to 20° C. to precipitate the Z-Gly-MePro-Glu-OH. The mixture was filtered and the solid was washed with 192 eq of water before drying at about 25° C. for 2.5 days. The solid was then solubilized at 64° C. by addition of 55 eq of water and 31 eq of iPrOH. After solubilization, the mixture was diluted with 275 eq of water and cooled to 10° C. for crystallization. The mixture was filtered and the solid was washed with 60 eq of water before drying at 27° C. (Z-Gly-MePro-Glu-OH dried product—Purity: 99.6%; NMR assay: 98%; Yield 74%).

Procedure 3E

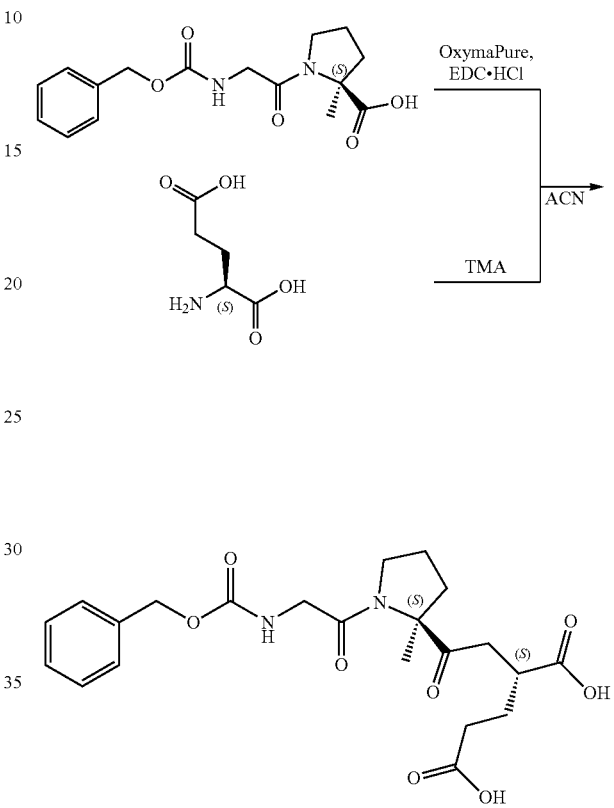

In reactor 1, H-Glu-OH (1.05 eq) was suspended in ACN (about 2.2 eq). TMA (about 3.5 eq) added, and the mixture was heated to dissolve solids. After dissolution, the solution was cooled to room temperature. In reactor 2, Z-Gly-MePro-OH (1 eq) was suspended in ACN (14 eq). Oxyma Pure (1 eq) and EDC·HCl (1 eq) were added. The mixture was stirred at room temperature until the solids dissolved. The contents of reactor 2 were added to reactor 1. The conversion from Z-Gly-MePro-OH to Z-Gly-MePro-Glu-OH was monitored by HPLC. Upon completion the reaction mixture was added to an aqueous solution comprised of KHSO₄ (about 2.5 wt %) dissolved in about 100 eq H₂O. ACN was removed from the aqueous suspension of Z-Gly-MePro-Glu-OH by vacuum distillation with H₂O. After stirring at room temperature, the product in the resulting suspension was isolated by filtration and washed with water. The solid obtained was dissolved in an aqueous solution comprised of NaHCO₃ (about 5 wt %) in 110 eq H₂O, and recrystallized by addition of an aqueous solution comprised of KHSO₄ (about 10 wt %) in 90 eq H₂O. The product was isolated by filtration, washed with water, and dried under vacuum at 45° C. Z-Gly-MePro-Glu-OH (75% yield) was obtained.

Step 4: Deprotection and Isolation of Trofinetide
Several alternative procedures can be used in this step.
Procedure 4A

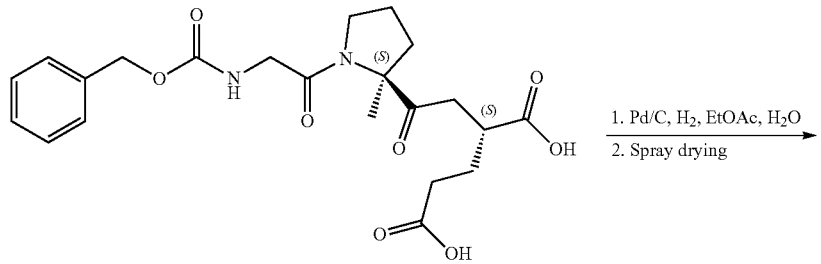

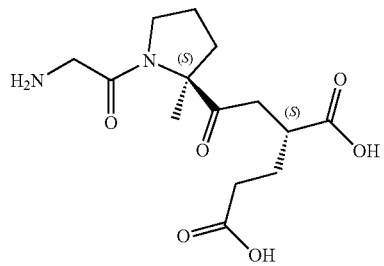

30

Z-Gly-MePro-Glu-OH (1 eq) was suspended in water (about 25 eq) and EtOAc (about 15 eq). Pd/C (0.025 eq by weight and containing 10% Pd by weight) was added, and the reaction mixture hydrogenated by bubbling hydrogen through the reaction mixture at room temperature. The conversion from Z-Gly-MePro-Glu-OH to trofinetide was monitored by HPLC, and upon reaction completion the catalyst was removed by filtration, and the layers separated. Residual EtOAc was removed from the aqueous solution containing trofinetide by sparging with nitrogen or washing with heptane. The aqueous solution was spray-dried to isolate the product. Trofinetide (90% yield) was obtained. Alternatively, deprotection can be accomplished using MeOH only, or a combination of iPrOH and MeOH, or by use of ethyl acetate in water.

Procedure 4B

This Procedure is for a variant of Procedure 4A, excluding EtOAc. Z-Gly-MePro-Glu-OH (1 eq) was suspended in water (about 50 eq). Pd/C (0.05 eq, 5% Pd by weight) was added, and the reaction mixture hydrogenated at room temperature with a pressure of 5 bar. The conversion from Z-Gly-MePro-Glu-OH to trofinetide was monitored by HPLC. Upon reaction completion the catalyst was removed by filtration, and the aqueous layer washed with EtOAc (about 5 eq). Residual EtOAc was removed from the aqueous solution containing trofinetide by sparging with nitrogen or washing with heptane. The aqueous solution was spray-dried to isolate the product. Trofinetide (90% yield) was obtained.

Procedure 4C

This Procedure is for a variant of Procedure 4A, replacing EtOAc with MeOH. Z-Gly-MePro-Glu-OH (1 eq) was suspended in MeOH (100 eq) and water (12 eq). Pd/Si (0.02 eq by weight) was added and the mixture was heated at 23° C. for the hydrogenolysis. Solubilization of the peptide occurred during the deprotection. The conversion from Z-Gly-MePro-Glu-OH to trofinetide was monitored by HPLC, and upon reaction completion the catalyst was removed by filtration and the layers were washed with MeOH and iPrOH. The solvents were concentrated under vacuum at 45° C., and trofinetide precipitated. The precipitate was filtered and dried at 45° C. to provide trofinetide.

Procedure 4D

This Procedure is for a variant of Procedure 4A, replacing Pd/C with Pd/Si. One (1.0) eq of Z-Gly-MePro-Glu-OH was partially solubilized in 105 eq of MeOH and 12 eq of water. Pd/Si (0.02 eq by weight) was added and the mixture was heated at 23° C. for the hydrogenolysis. Solubilization of the peptide occurred during the deprotection. At the end of the deprotection (conversion rate approximately 99% after 1 hr), the catalyst was filtered off and washed with 20-30 eq of MeOH. iPrOH (93 eq) was added and MeOH was replaced by iPrOH by concentration at 45° C. under vacuum. The peptide was concentrated until it began to precipitate. The peptide was filtered and dried at 45° C. (H-Gly-MePro-Glu-OH dried product: Purity: 98.1%; NMR assay: 90%; Yield 81%).

Procedure 4E

This Procedure is for a variant of Procedure 4A, removing $H_2O$ and replacing Pd/C with Pd/Si. One (1.0) eq of Z-Gly-MePro-Glu-OH was partially solubilized in 44 eq of MeOH. Pd/Si type 340 (0.02 eq by weight) was added and the mixture was kept at 20° C. for the hydrogenolysis. Solubilization of the peptide occurred during the deprotection. At the end of the deprotection (conversion rate about 99.9%, after 3-3.5 hrs), the catalyst was filtered off and washed with 8 eq of MeOH. Deprotected peptide was then precipitated in 56 eq of iPrOH. After 30 min at 5° C., the peptide was filtered and washed with three times with 11 eq of iPrOH before drying at 25° C. (H-Gly-MePro-Glu-OH dried product: Purity: 99.4%; HPLC assay: ~98%; Yield: 81%).

Procedure 4F

This Procedure is for a variant of Procedure 4A. One (1) eq of Z-Gly-MePro-Glu-OH was partially solubilized in 14 eq of EtOAc and 25 eq of water. Pd/C (0.01 eq by weight)

was added and the mixture was kept at 20° C. for the hydrogenolysis. Solubilization of the peptide occurred during the deprotection. At the end of the deprotection (conversion rate about 100%, after about 3.5 hrs), the catalyst was filtered off and washed with a mixture of 3.5 eq of EtOAc and 6 eq of water. The aqueous layer was then ready for spray-drying (Aqueous H-Gly-MePro-Glu-OH peptide solution: Purity: 98.6%; Yield: —95%).

Procedure 4G

This Procedure is for a variant of Procedure 4A, replacing Pd/C with Pd/Si, EtOAc with MeOH, and removing $H_2O$. Pd/Si type 340 (0.02 eq by weight) was added to 2.9 vols of MeOH for pre-reduction during 30 min. One (1.0) eq of Z-Gly-MePro-Glu-OH was partially solubilized in 34 eq of MeOH. The reduced palladium was then transferred to the peptide mixture. The mixture was kept at 20° C. for the hydrogenolysis. Solubilization of the peptide occurred during the deprotection. Pd/C type 39 (0.007 eq by weight) was added to the mixture to increase reaction kinetics. At the end of the deprotection, the catalyst was filtered off and washed with 13.6 eq of MeOH. The deprotected peptide was then precipitated in 71 eq of iPrOH. After about 40 min, the peptide was filtered and washed with 35 eq of iPrOH. The peptide was dried below 20° C. and was then ready for solubilization in water and spray-drying.

Procedure 4H

This Procedure is for a variant of Procedure 4A. One (1.0) eq of Z-Gly-MePro-Glu-OH was partially solubilized in 24.8 eq of water and 13.6 eq of EtOAc. Pd/C type 39 (0.025 eq by weight) was added to the peptide mixture. The mixture was kept at 20° C. for the hydrogenolysis. Solubilization of the peptide occurred during the deprotection. At the end of the deprotection (19 hrs), the catalyst was removed by filtration and washed with 5.3 eq of water and 2.9 eq of EtOAc. The biphasic mixture was then decanted to remove the upper organic layer. The aqueous layer was diluted with water to reach an H-Gly-MePro-Glu-OH concentration suitable for spray-drying the solution.

Example 2: Alternative Trofinetide Manufacturing Process

An alternative method for synthesis of Trofinetide is based on U.S. Pat. No. 8,546,530 adapted for a tripeptide as follows.

The persilylated compounds used to synthesis Formula (Ia) (trofinetide) are obtained by silylating a corresponding peptide or amino acid by reaction with a silylating agent, optionally in an organic solvent. The persilylated peptide or amino acid can be isolated and purified if desired. One can use the persilylated peptide or amino acid in situ, e.g. by combining a solution containing persilylated peptide or amino acid with a solution containing, optionally activated, peptide or amino acid.

In step 2, the persilylated compound of an amino acid is obtained by silylating a corresponding amino acid (for example, H-MePro-OH) by reaction with a silylating agent, optionally in an organic solvent. The persilylated amino acid can be isolated and purified if desired. One can use the persilylated amino acid in situ, e.g. by combining a solution containing the persilylated amino acid with a solution containing, optionally activated, amino acid (for example, Z-Gly-OH).

In step 3, the persilylated compound of an amino acid is obtained by silylating a corresponding amino acid (for example, H-Glu-OH) by reaction with a silylating agent, optionally in an organic solvent. The persilylated amino acid or peptide can be isolated and purified if desired. It is however useful to use the persilylated amino acid or peptide in situ, e.g. by combining a solution containing the persilylated amino acid with a solution containing, optionally activated (for example, by using EDC·HCl and Oxyma Pure), peptide (for example, Z-Gly-MePro-OH).

In the present invention, it is useful to use silylating agents, such as N-trialkylsilyl amines or N-trialkylsilyl amides, not containing a cyano group. Examples of such silylating reagents include N,O-bis(trimethylsilyl)acetamide (BSA), N,O-bis(trimethylsilyetrifluoroacetamide, hexamethyldisilazane, N-methyl-N-(trimethylsilyl)acetamide (TMA), N-methyl-N-(trimethylsilyl)trifluoroacetamide, N-(trimethylsilyl)acetamide, N-(trimethylsilyl)diethylamine, N-(trimethylsilyl)dimethylamine, 1-(trimethylsilyl)imidazole, 3-(trimethylsilyl)-2-oxazolidone.

The reaction of step 2 is generally carried out at a temperature from 0° C. to 100° C., optionally from 10° C. to 40° C., and optionally from 15° C. to 30° C.

The reaction of step 3 is generally carried out at a temperature from 0° C. to 100° C., optionally from 10° C. to 60° C., optionally from 15° C. to 50° C.

In the reaction of step 2, generally 0.5 to 5 equivalents, optionally 1 to 3 equivalents, optionally about 1.5 to 2.5 equivalents of silylating agent are used relative to the molar amount of functional groups to be silylated. Use of 2 to 4 equivalents of silylating agent relative to the molar amount of functional groups to be silylated is also possible. "Functional groups to be silylated" means particular groups having an active hydrogen atom that can react with the silylating agent such as amino, hydroxyl, mercapto or carboxyl groups.

In the reaction of step 3, generally 0.5 to 5 equivalents, optionally 2 to 4.5 equivalents, optionally about 3 to 4 equivalents of silylating agent are used relative to the molar amount of functional groups to be silylated. Use of 2.5 to 4.5 equivalents of silylating agent relative to the molar amount of functional groups to be silylated is also possible.

It is understood that "persilylated" means an amino acid or peptide or amino acid analogue or peptide analogue in which the groups having an active hydrogen atom that can react with the silylating agent are sufficiently silylated to ensure that a homogeneous reaction medium for a coupling step is obtained.

In the process according to the invention, the reaction between the amino acid or peptide and the persilylated amino acid or peptide is often carried out in the presence of a carboxyl group activating agent. In that case the carboxylic activating reagent is suitably selected from carbodiimides, acyl halides, phosphonium salts and uronium or guanidinium salts. More optionally, the carboxylic activating agent is an acyl halide, such as isobutyl chloroformate or pivaloyl chloride or a carbodiimide, such as EDC·HCl or DCC.

Good results are often obtained when using additional carboxylic activating reagents which reduce side reactions and/or increase reaction efficiency. For example, phosphonium and uronium salts can, in the presence of a tertiary base, for example, N,N-diisopropylethylamine (DIPEA) and triethylamine (TEA), convert protected amino acids into activated species. Other reagents help prevent racemization by providing a protecting reagent. These reagents include carbodiimides (for example, DCC) with an added auxiliary nucleophile (for example, 1-hydroxy-benzotriazole (HOBt), 1-hydroxy-azabenzotriazole (HOAt), or Suc-OH) or derivatives thereof. Another reagent that can be utilized is TBTU.

The mixed anhydride method, using isobutyl chloroformate, with or without an added auxiliary nucleophile, is also used, as is the azide method, due to the low racemization associated with it. These types of compounds can also increase the rate of carbodiimide-mediated couplings. Typical additional reagents include also bases such as N,N-diisopropylethylamine (DIPEA), triethylamine (TEA) or N-methylmorpholine (NMM).

When the silylation is carried out in the presence of a solvent, said solvent is optionally a polar organic solvent, more optionally a polar aprotic organic solvent. An amide type solvent such as N,N-dimethylformamide (DMF) or N,N-dimethylacetamide (DMAC) can be used. In the present invention for step 2, one can use an alkyl acetate solvent, in particular ethyl acetate is more particularly optional.

In the present invention for step 3, one can use a chlorinated hydrocarbon solvent or alkyl cyanide solvent, in particular dichloromethane or acetonitrile are more particularly optional.

In another embodiment, silylation is carried out in a liquid silylation medium consisting essentially of silylating agent and amino acid or peptide.

In the present invention, amino acid or peptide is understood to denote in particular an amino acid or peptide or amino acid analogue or peptide analogue which is bonded at its N-terminus or optionally another position, to a carboxylic group of an amino protected amino acid or peptide.

Example 3: Specifications for Compositions Containing Compounds of Formula (I)

| Analyses | Specification |
|---|---|
| Appearance | White to off-white powder |
| Identification by LC | RRT 1.00 +/− 0.02 versus reference standard |
| Assay by LC on dried basis | 97%-100% w/w |
| Total Impurities | NMT 2% w/w |
| Single Unidentified Impurities | <0.05% w/w |
| Single Identified Impurities | ≤0.05% or qualification level (% w/w) |
| Z-Gly-MePro-Glu-OH | ≤0.3% w/w |
| Water Content | NMT 7.5% w/w |
| Residual Solvents | Comply with ICH Q3C[1] |

[1]ICH guideline Q3C on impurities: guideline for residual solvents

Example 4: Alternative Manufacturing of Trofinetide Example 1, Step 4, Procedure 4B This Procedure is for a variant of Step 4, Procedure 4B. Z-Gly-MePro-Glu-OH (1 eq) was added in portions to Pd/C (0.027 eq by weight and containing 5% Pd by weight) in about 50 eq of water. The reaction mixture was hydrogenated at 20° C. at a pressure of 5 bar for at least 4 cycles of 4 hrs each. Pd/C (0.0027 eq by weight) was charged between cycles, as needed, to speed up the reaction. The conversion from Z-Gly-MePro-Glu-OH to trofinetide was monitored by HPLC. Upon reaction completion the catalyst was removed by filtration, washed with water (12.5 eq) and the aqueous layer washed with EtOAc (about 14 eq). After phase separation, residual EtOAc was removed from the aqueous solution containing trofinetide by sparging with nitrogen under vacuum at 20° C. for about 3 hrs. The aqueous solution was filtered. The final concentration of trofinetide was about 25 wt % and the solution was then ready for spray-drying to isolate the product.

Example 5: Alternative Composition of Trofinetide

A composition comprising a compound of Formula (I)

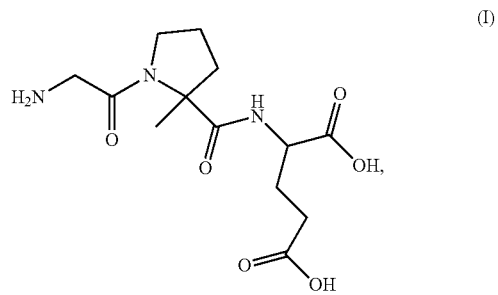 [SMILES: CC1(C(=O)NC(CCC(=O)O)C(=O)O)CCCN1C(=O)CN]

(I)

or a stereoisomer, hydrate, or pharmaceutically acceptable salt thereof, and a compound of Formula (II):

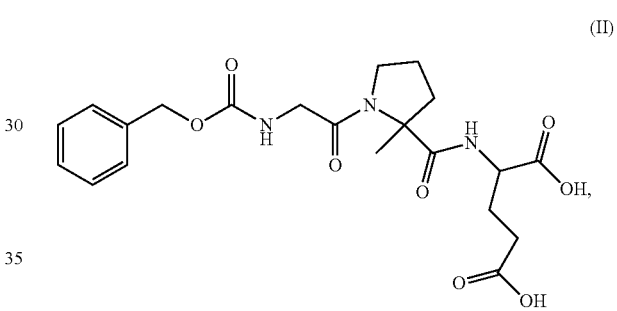

(II)

or a stereoisomer, hydrate, or pharmaceutically acceptable salt thereof, and/or a compound of Formula (III):

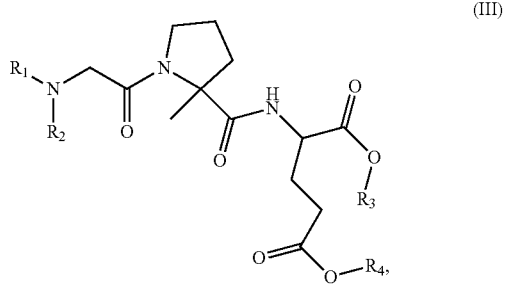

(III)

or a stereoisomer, hydrate, or pharmaceutically acceptable salt thereof, wherein $R_1$, $R_2$, $R_3$ and $R_4$ independently are selected from the group consisting of hydrogen and $C_{1-4}$ alkyl, provided that least one of $R_1$, $R_2$, $R_3$ and $R_4$ is $C_{1-4}$ alkyl, and wherein the composition comprises at least 90 wt %, such as 91 wt %, 92 wt %, 93 wt %, 94 wt %, 95 wt %, 96 wt %, or 97 wt % of the compound of Formula (I) on an anhydrous basis.

Example 6: Alternative Composition of Trofinetide

A composition comprising a compound of Formula (Ia)

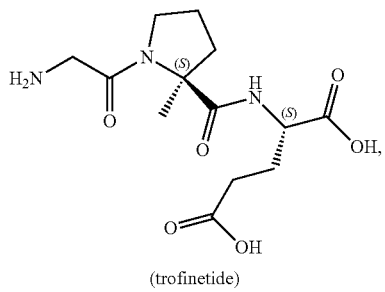
(trofinetide)

(Ia)

or a hydrate, or pharmaceutically acceptable salt thereof, and a compound of Formula (II):

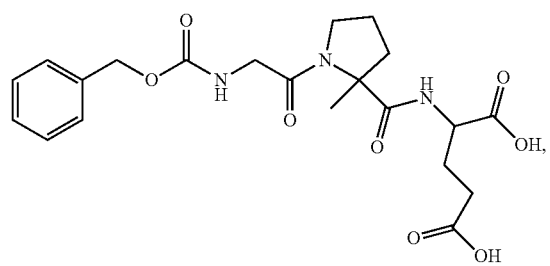

(II)

or a stereoisomer, hydrate, or pharmaceutically acceptable salt thereof, and/or a compound of Formula (III):

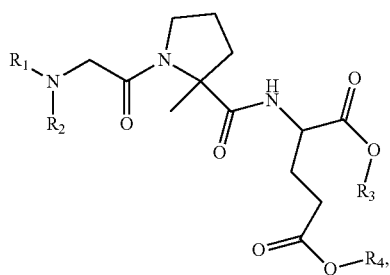

(III)

or a stereoisomer, hydrate, or pharmaceutically acceptable salt thereof, wherein $R_1$, $R_2$, $R_3$ and $R_4$ independently are selected from the group consisting of hydrogen and $C_{1-4}$ alkyl, provided that least one of $R_1$, $R_2$, $R_3$ and $R_4$ is $C_{1-4}$ alkyl, and wherein the composition comprises at least 90 wt %, such as 91 wt %, 92 wt %, 93 wt %, 94 wt %, 95 wt %, 96 wt %, or 97 wt % of the compound of Formula (Ia) on an anhydrous basis.

Example 7: A Product of Trofinetide

A product, including a kit containing a dosage form with instructions for use, comprising a compound of Formula (Ia)

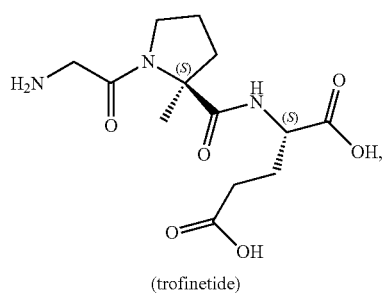
(trofinetide)

(Ia)

or a hydrate, or pharmaceutically acceptable salt thereof, and a compound of Formula (IIa)

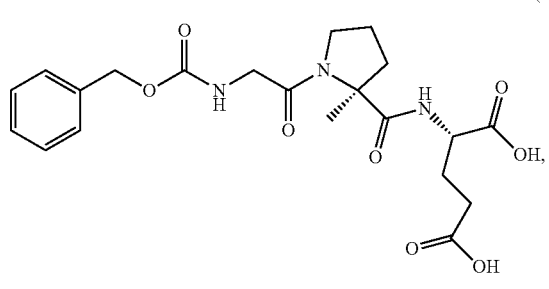
(Z-Gly-MePro-Glu-OH)

(IIa)

or a hydrate, or pharmaceutically acceptable salt thereof, wherein the product comprises between 95 wt % and 105 wt %, such as 96 wt %, 97 wt %, 98 wt %, 99 wt %, 100 wt %, 101 wt %, 102 wt %, 103 wt %, or 104 wt % of the specified amount of the compound of Formula (Ia) in the product.

Example 8: A Product of Trofinetide

A product, including a kit containing a dosage form with instructions for use, comprising a compound of Formula (Ia)

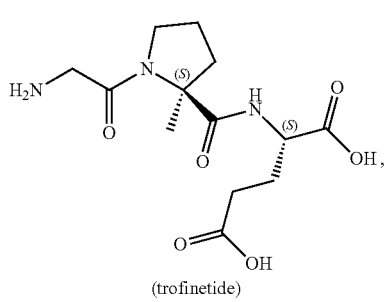
(trofinetide)

(Ia)

or a hydrate, or pharmaceutically acceptable salt thereof, and a compound of Formula (IIa)

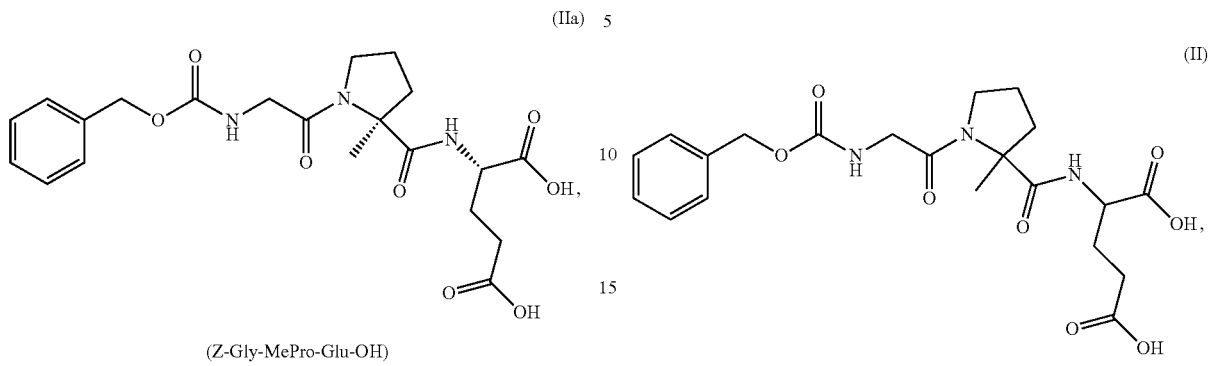

(Z-Gly-MePro-Glu-OH)

or a hydrate, or pharmaceutically acceptable salt thereof, and additionally comprising one or more compounds selected from the group consisting of Formula (III), Formula (IIIa), Formula (IV), Formula (V), Formula (VI), Formula (VII), Formula (VIII), and Formula (IX), wherein the composition comprises between 95 wt % and 105 wt %, such as 96 wt %, 97 wt %, 98 wt %, 99 wt %, 100 wt %, 101 wt %, 102 wt %, 103 wt %, or 104 wt % of the specified amount of the compound of Formula (Ia) in the product.

Example 9: Analysis of Products and Compositions

The products and compositions disclosed herein may be analyzed by liquid chromatography, a suitable chromatographic method using UPLC, e.g. using materials and conditions such as Waters Acquity CSH C18, 1.7 μm, 150×2.1 mm column, water with 0.1% TFA (mobile phase A), and water/ACN 70/30+0.1% TFA (mobile phase B), ranging from (4% phase A/6% phase B to 100% phase B and flushed with 4% phase A/6% phase B). Flow rate: 0.35 ml/min, Column temperature: 40° C., autosampler temperature: 4° C., injection volume: 4 μl (e.g. prepared by weighing about 10 mg of powder in a 10 ml volumetric flask and diluted to volume with water). Examples of detectors are UV (ultraviolet, UV 220 nm) and MS (mass spectrometry).

INDUSTRIAL APPLICABILITY

This invention finds use in the pharmaceutical, medical, and other health care fields.

What is claimed is:

1. A composition comprising a compound of Formula (I):

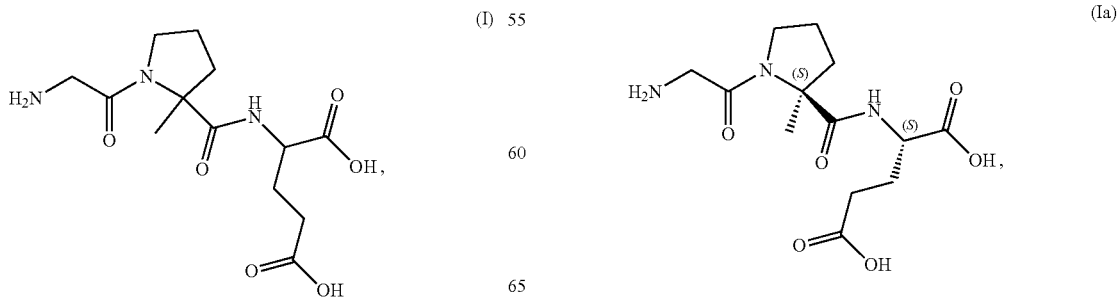

or a stereoisomer, or pharmaceutically acceptable salt thereof, and between about 0.001 wt % and about 2 wt % of a compound of Formula (II):

or a stereoisomer, or pharmaceutically acceptable salt thereof, and between about 0.001 wt % and about 2 wt % of a compound of Formula (III):

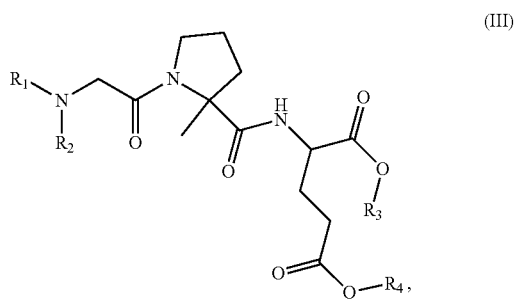

or a stereoisomer, or pharmaceutically acceptable salt thereof, wherein $R_1$, $R_2$, $R_3$ and $R_4$ independently are selected from the group consisting of hydrogen and $C_{1-4}$ alkyl, provided at least one of $R_1$, $R_2$, $R_3$ and $R_4$ is $C_{1-4}$ alkyl.

2. The composition according to claim 1, wherein the compound of Formula (I) is a compound of Formula (Ia):

or pharmaceutically acceptable salt thereof.

3. The composition according to claim 1, wherein the compound of Formula (II) is a compound of Formula (IIa):

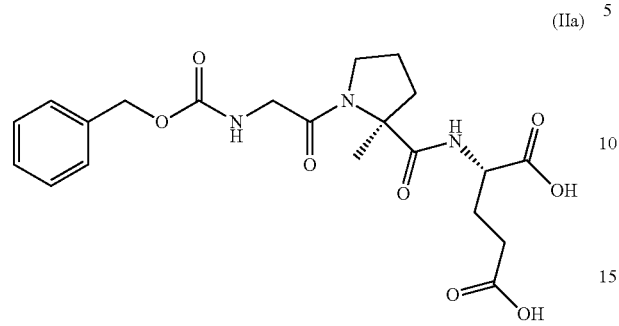

(IIa)

or pharmaceutically acceptable salt thereof.

4. The composition according to claim 1, wherein the compound of Formula (III) is a compound of Formula (IX):

(IX)

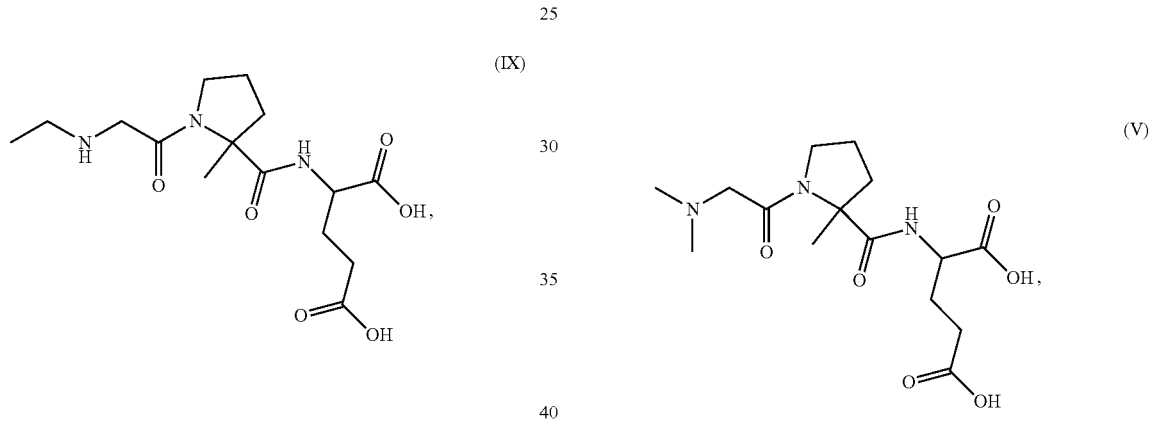

or pharmaceutically acceptable salt thereof.

5. The composition according to claim 1, comprising the compound of Formula (III), wherein the compound according to Formula (III) is a compound of Formula (IIIa):

(IIIa)

or pharmaceutically acceptable salt thereof.

6. The composition according to claim 2 comprising between about 97 wt % and about 100 wt % of the compound of Formula (Ia) on an anhydrous basis.

7. The composition according to claim 1, wherein the compound according to Formula (III) is a compound of Formula (IV):

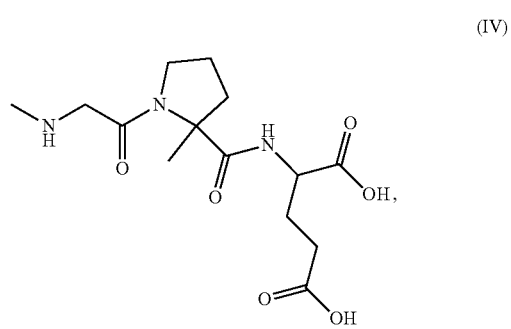 [SMILES: CNCC(=O)N1CCCC1(C)C(=O)NC(CCC(=O)O)C(=O)O]

(IV)

or a stereoisomer, or pharmaceutically acceptable salt thereof;

Formula (V):

(V)

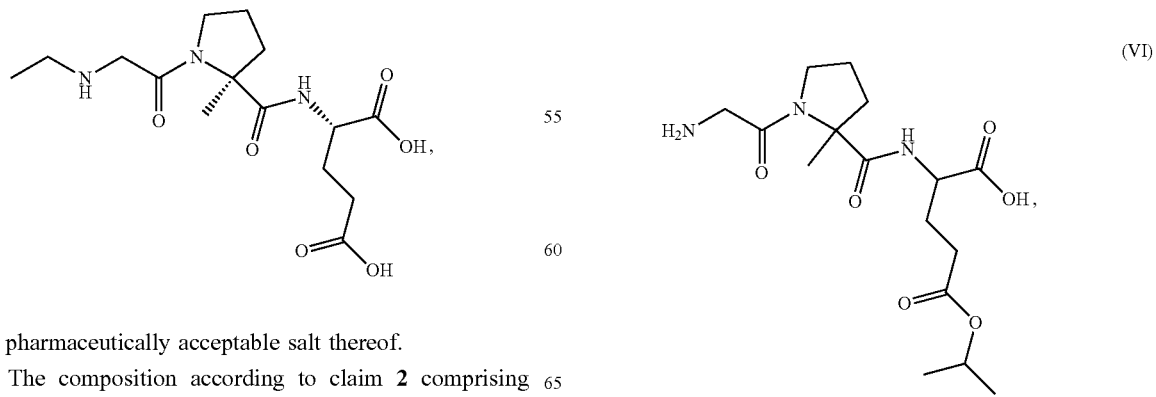

or a stereoisomer, or pharmaceutically acceptable salt thereof;

Formula (VI):

(VI)

or a stereoisomer, or pharmaceutically acceptable salt thereof;

Formula (VII):

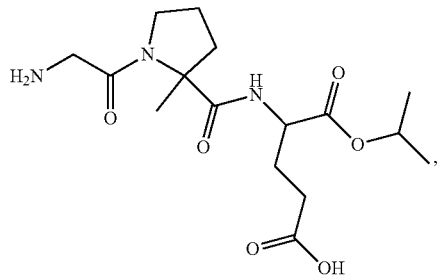

(VII)

or a stereoisomer, or pharmaceutically acceptable salt thereof;

Formula (VIII):

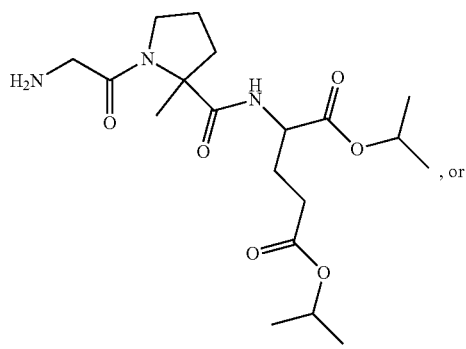

(VIII)

, or or a stereoisomer, or pharmaceutically acceptable salt thereof;

Formula (IX):

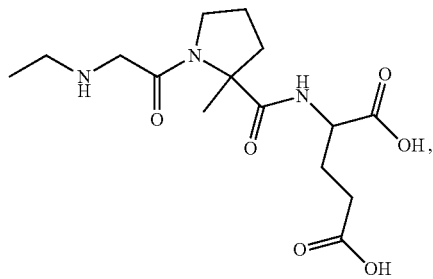

(IX)

or a stereoisomer, or pharmaceutically acceptable salt thereof.

8. The composition according to claim 2, wherein said composition is obtained by:
   a) coupling (2S)-2-methylpyrrolidine-2-carboxylic acid and benzyloxycarbonyl-glycine in the presence of an activating reagent, silylating agent and a solvent, or
   b) coupling benzyloxycarbonyl-glycine and N-hydroxysuccinimide and then coupling the obtained benzyloxycarbonyl-glycine N-succinimidyl ester and (2S)-2-methylpyrrolidine-2-carboxylic acid in the absence or presence of an activating reagent, a solvent and in the absence or presence of a silylating agent;
   c) coupling the obtained ((S)-1-(((benzyloxy)carbonyl) glycyl)-2-methylpyrrolidine-2-carboxylic acid) and (2S)-2-aminopentanedioic acid in the presence of an activating reagent, silylating agent and a solvent;
   d) obtaining ((S)-1-(((benzyloxy)carbonyl)glycyl)-2-methylpyrrolidine-2-carbonyl)-L-glutamic acid; and
   e) deprotecting ((S)-1-(((benzyloxy)carbonyl)glycyl)-2-methylpyrrolidine-2-carbonyl)-L-glutamic acid, to obtain a composition comprising the compound of Formula (Ia).

9. The composition according to claim 8, wherein the compound according to Formula (II) is a compound of Formula (IIa):

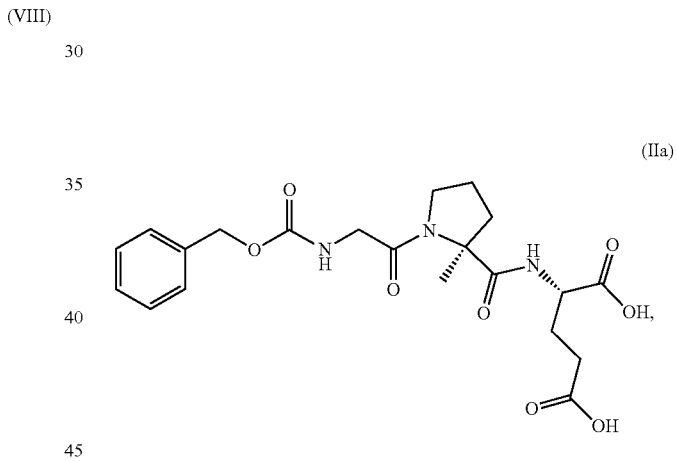

(IIa)

or pharmaceutically acceptable salt thereof.

10. The composition according to claim 8, wherein deprotecting is achieved by hydrogenation.

11. The composition according to claim 10, wherein hydrogenation is performed in the presence of a Pd/C catalyst.

12. The composition according to claim 10, wherein hydrogenation is performed in the presence of a Pd/Si catalyst.

13. The composition according to claim 10, wherein the hydrogenation is performed using at least one solvent selected from the group consisting of water, ethyl acetate, isopropyl acetate, methanol, ethanol, isopropanol, or mixtures thereof.

14. A kit containing a dosage form comprising a compound of Formula (Ia):

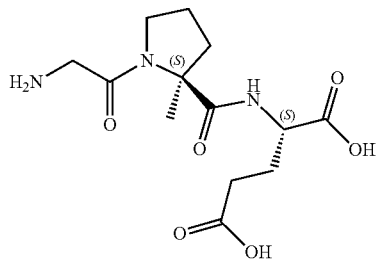
(Ia)

or a pharmaceutically acceptable salt thereof, and between about 0.001 wt % and about 2 wt % of a compound of Formula (IIa):

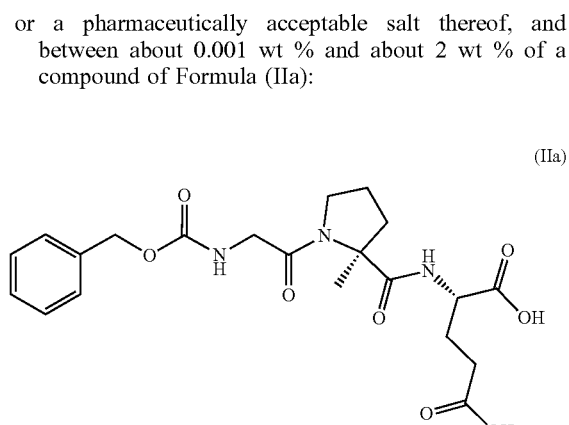
(IIa)

or pharmaceutically acceptable salt thereof, and instructions for administration to a subject in need thereof.

15. The composition according to claim 1, wherein the compound of Formula (II), or stereoisomer, or pharmaceutically acceptable salt thereof, is present in an amount between about 0.001 wt % and about 0.2 wt %; and the compound of Formula (III), or stereoisomer, or pharmaceutically acceptable salt thereof, is absent.

16. A composition according to claim 1, comprising a compound of Formula (Ia):

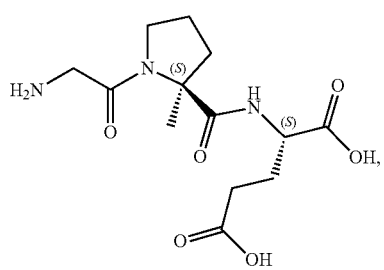
(Ia)

or pharmaceutically acceptable salt thereof, between about 0.001 wt % and about 0.2 wt % of a compound of Formula (IIa):

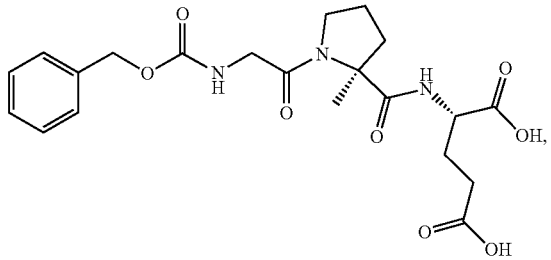
(IIa)

or pharmaceutically acceptable salt thereof; and between about 0.001 wt % and about 0.2 wt % of a compound of Formula (IIIa):

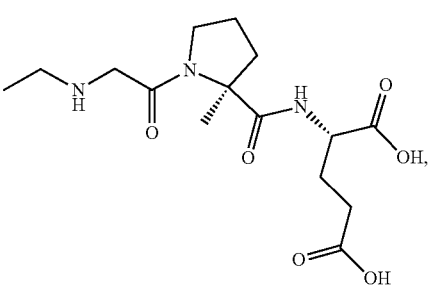
(IIIa)

or pharmaceutically acceptable salt thereof.

17. A composition comprising a compound of Formula (I):

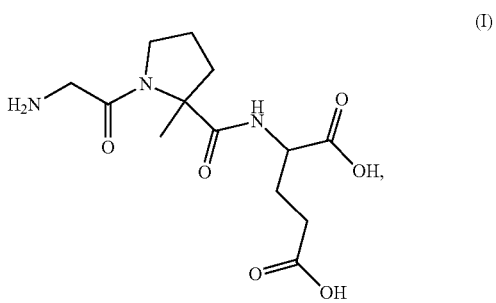 [SMILES: CC1(C(=O)NC(CCC(=O)O)C(=O)O)CCCN1C(=O)CN]
(I)

or a stereoisomer, or pharmaceutically acceptable salt thereof, and between about 0.001 wt % and about 2 wt % of a compound of Formula (III):

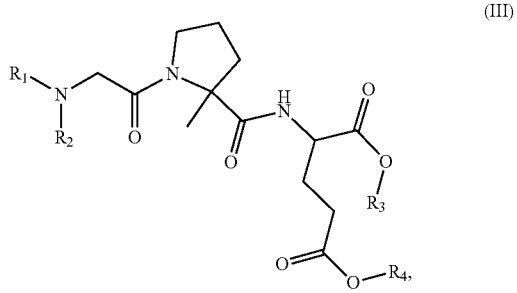
(III)

or a stereoisomer, or pharmaceutically acceptable salt thereof, wherein R$_1$, R$_2$, R$_3$ and R$_4$ independently are selected from the group consisting of hydrogen and C$_{1-4}$ alkyl, provided at least one of R$_1$, R$_2$, R$_3$ and R$_4$ is C$_{1-4}$ alkyl.

18. The composition according to claim 17, wherein the compound of Formula (I) is a compound of Formula (Ia):

(Ia)

or pharmaceutically acceptable salt thereof.

19. The composition according to claim 17, wherein the compound according to Formula (III) is a compound of Formula (IV):

(IV)

or a stereoisomer, or pharmaceutically acceptable salt thereof;

Formula (V):

(V)

or a stereoisomer, or pharmaceutically acceptable salt thereof;

Formula (VI):

(VI)

or a stereoisomer, or pharmaceutically acceptable salt thereof;

Formula (VII):

(VII)

or a stereoisomer, or pharmaceutically acceptable salt thereof;

Formula (VIII):

(VIII)

or a stereoisomer, or pharmaceutically acceptable salt thereof; or

Formula (IX):
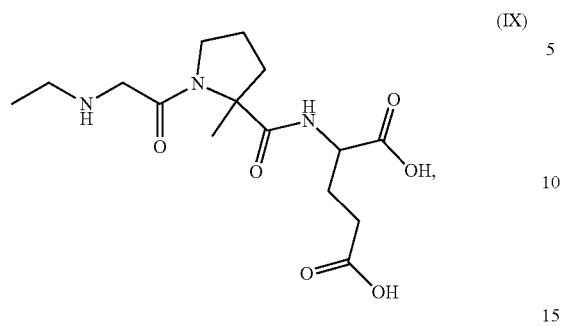
(IX)
or a stereoisomer, or pharmaceutically acceptable salt thereof.
20. The composition according to claim 17, wherein the compound of Formula (III), or stereoisomer, or pharmaceutically acceptable salt thereof, is present in an amount between about 0.001 wt % and about 0.2 wt %.
* * * * *